(12) United States Patent
Lu et al.

(10) Patent No.: US 10,124,073 B2
(45) Date of Patent: Nov. 13, 2018

(54) TARGETING PEPTIDES AND METHODS OF USE

(71) Applicant: CASE WESTERN RESERVE UNIVERSITY, Cleveland, OH (US)

(72) Inventors: Zheng-Rong Lu, Cleveland, OH (US); Zheng Han, Cleveland, OH (US); Hui Zhu, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 15/502,160

(22) PCT Filed: Aug. 4, 2015

(86) PCT No.: PCT/US2015/043668
§ 371 (c)(1),
(2) Date: Feb. 6, 2017

(87) PCT Pub. No.: WO2016/022597
PCT Pub. Date: Feb. 11, 2016

(65) Prior Publication Data
US 2017/0224848 A1    Aug. 10, 2017

Related U.S. Application Data

(60) Provisional application No. 62/032,945, filed on Aug. 4, 2014.

(51) Int. Cl.
*A61K 49/00* (2006.01)
*A61K 49/14* (2006.01)
*G01N 33/574* (2006.01)

(52) U.S. Cl.
CPC ...... *A61K 49/0056* (2013.01); *A61K 49/0032* (2013.01); *A61K 49/0054* (2013.01); *A61K 49/14* (2013.01); *G01N 33/57492* (2013.01); *G01N 2333/78* (2013.01)

(58) Field of Classification Search
CPC .................................................. A61K 49/0056
See application file for complete search history.

(56) References Cited

U.S. PATENT DOCUMENTS

| | | | |
|---|---|---|---|
| 2012/0244070 A1 | 9/2012 | Lu et al. | |
| 2013/0011334 A1* | 1/2013 | Steuernagel | C07K 14/525 424/1.69 |
| 2017/0322213 A1* | 11/2017 | Choi | G01N 33/574 |
| 2018/0110886 A1* | 4/2018 | Lu | A61K 49/14 |

FOREIGN PATENT DOCUMENTS

| | | |
|---|---|---|
| EP | 3223016 A1 | 9/2017 |
| WO | 200175067 A2 | 10/2001 |
| WO | 2006026020 A2 | 3/2006 |
| WO | WO-2016-080633 A1 | 5/2016 |

OTHER PUBLICATIONS

Han et al.: "An EDB fibronectin specific contrast agent for molecular imaging of cancer metastasis", 23rd Annual Meeting & Exhibitjon May 30-Jun. 5, 2015 Proc. Intl. Soc. Mag. Reson. Med., vol. 23 Jun. 3, 2015 (Jun. 3, 2015).
Han et al.: "EDB Fibronectin Specific Peptide for Prostate Cancer Targeting", Bioconjugate Chemistry, vol. 26, No. 5, May 20, 2015 (May 20, 2015), pp. 830-83.
Wei et al.: "Screening and identifying of homing peptides to bladder cancer BIU-87 identifying of homing peptides to bladder cancer BIU-87 cells jn Chinese", Chin. J. Cancer Biother., vol. 20, rio. 5, Oct. 2013 (Oct. 2013), pp. 515-521.
Sun et al.: "MRI of Breast Tumor Initiating Cells Using the Extra Domain-B of Fibronectin Targeting Nanoparticles", THERANOSTICS , vol. 4, No. 8, Jan. 1, 2014 (Jan. 1, 2014), pp. 845-85.
Extended European Search Report for Application No. 15829365. 4-1453/3177638, 2018.
Supplementary European Search Report for Application No. 15829365. 4-1453/3177638, 2018.

* cited by examiner

*Primary Examiner* — Amber D Steele
(74) *Attorney, Agent, or Firm* — Tarolli, Sundheim, Covell & Tummino LLP

(57) ABSTRACT

A compound includes at least one targeting peptide coupled to a detectable moiety. The targeting peptide binds to EDB-FN or EDA-FN and includes at least one of amino acid sequence selected from the group consisting of SEQ ID NOs: 1-30.

22 Claims, 11 Drawing Sheets

Specification includes a Sequence Listing.

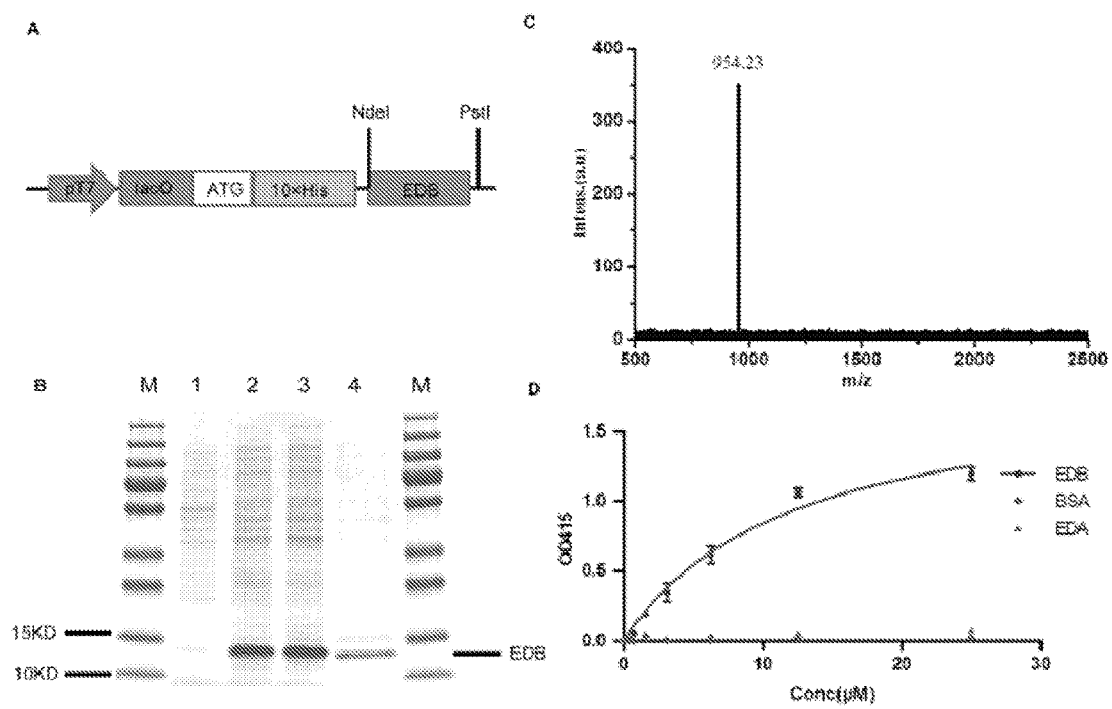
Figs. 1A-D
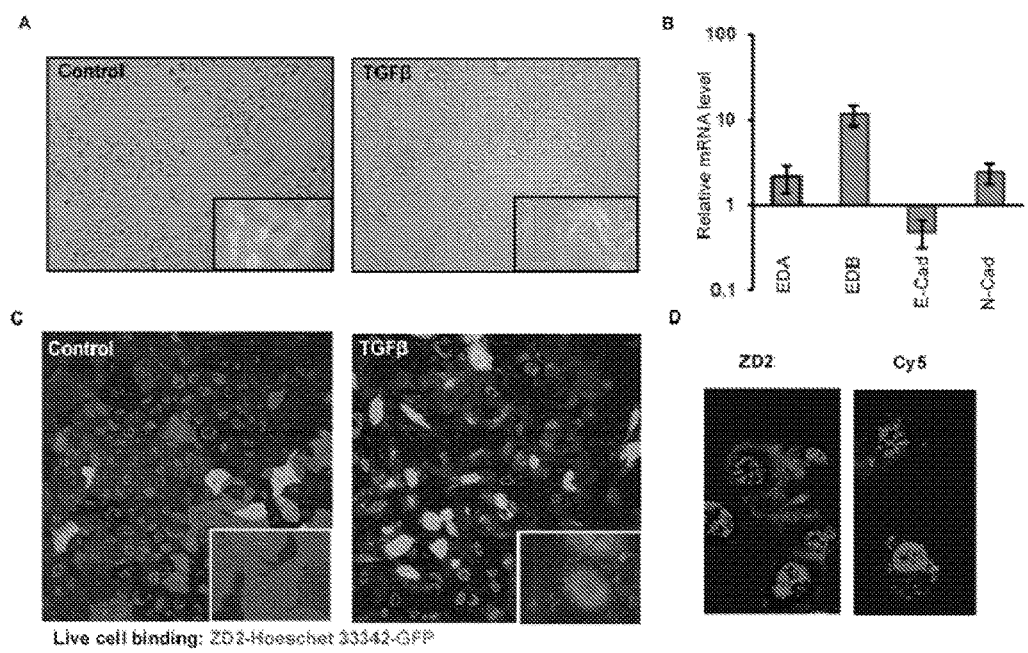
Figs. 2A-D

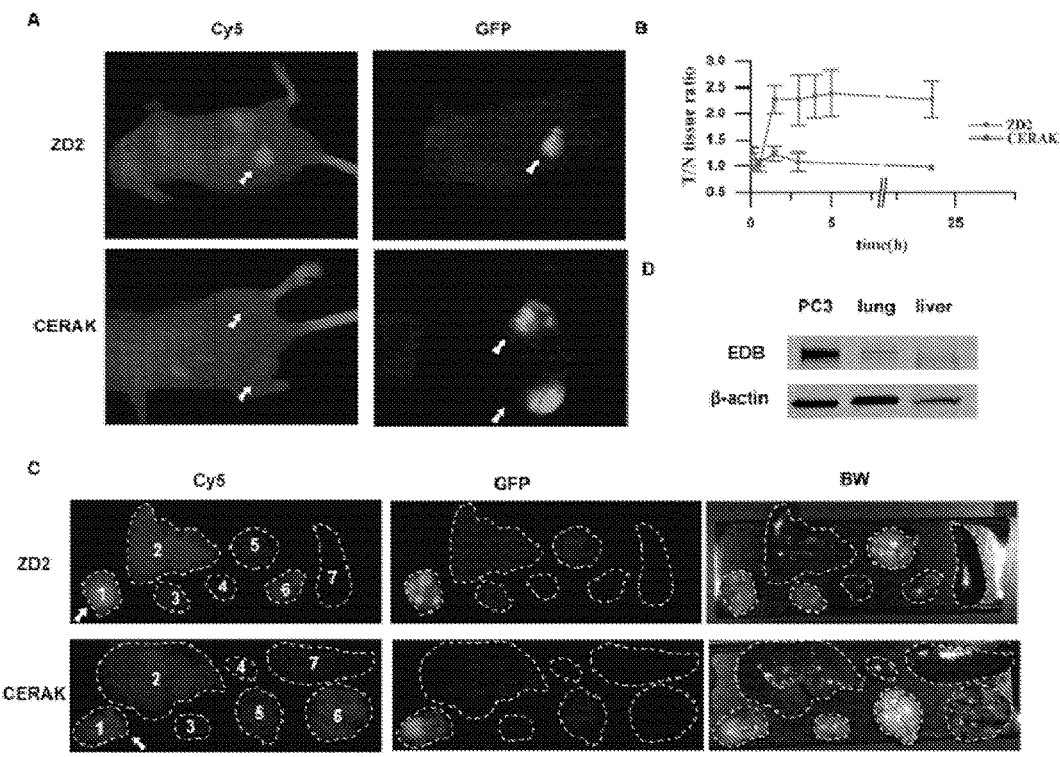
Figs. 3A-D
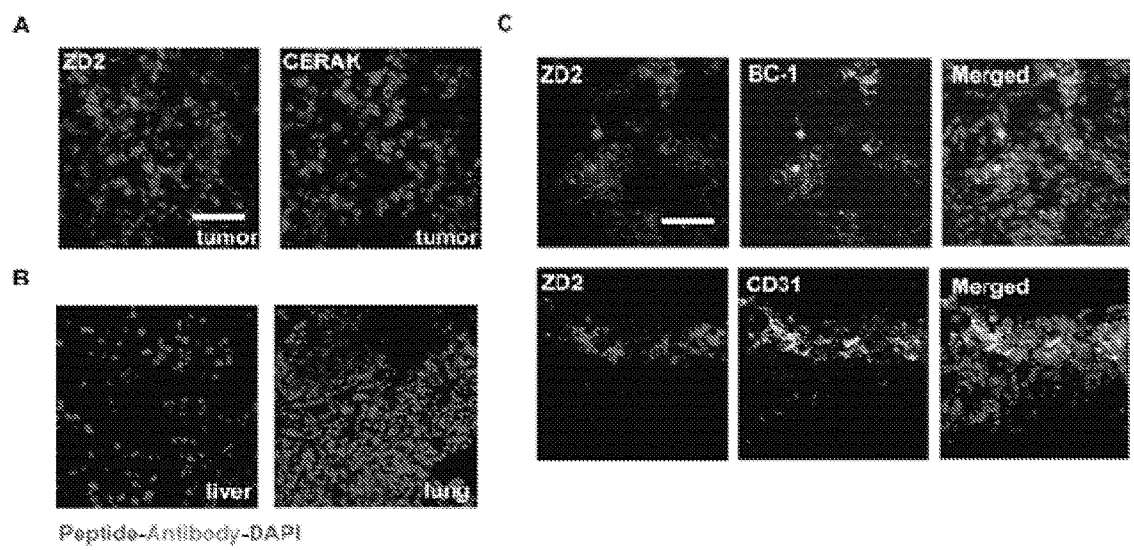
Figs. 4A-C

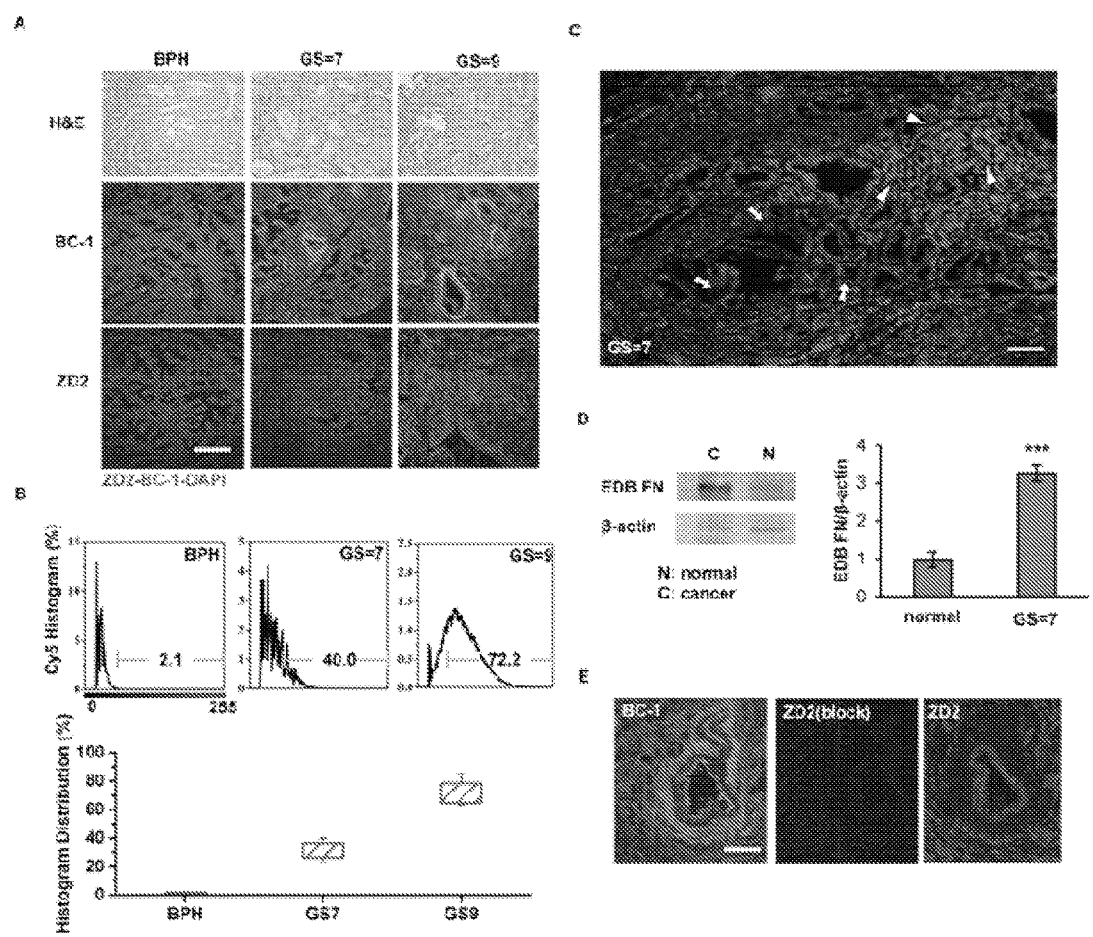
Figs. 5A-E

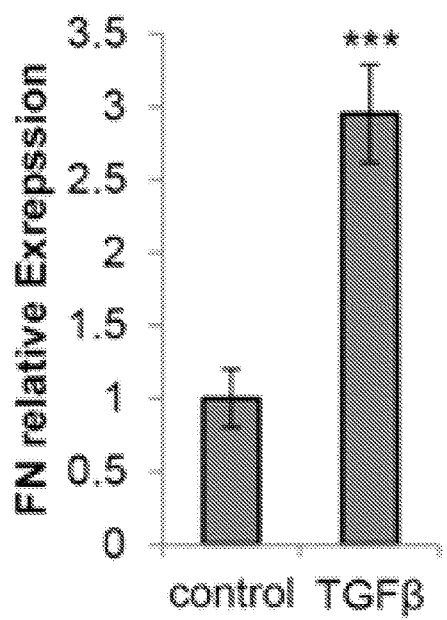
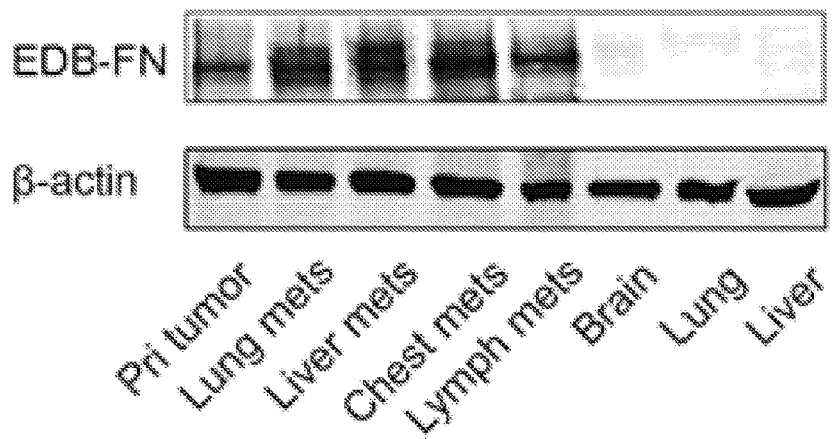
Figs. 6A-B

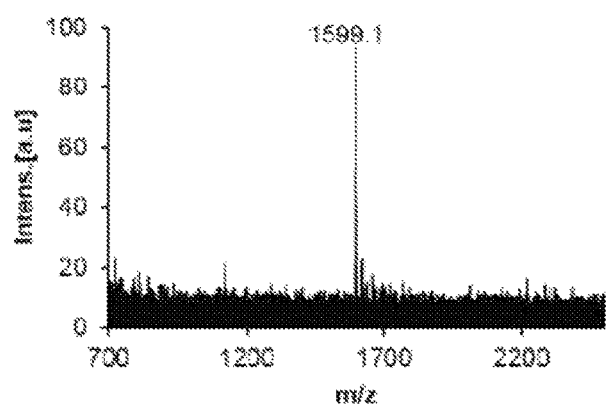
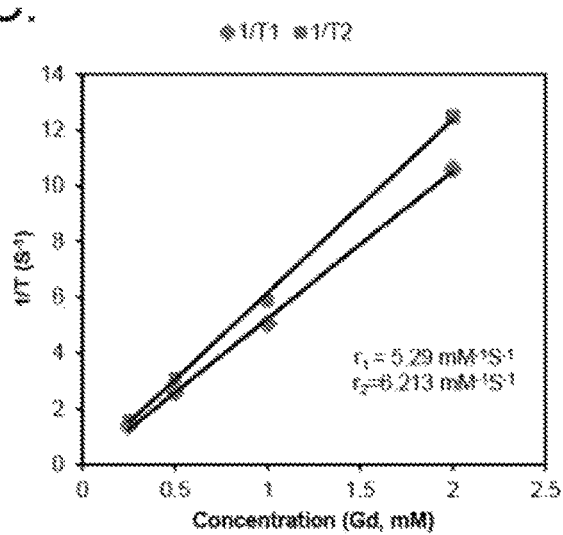
Figs. 7B-C

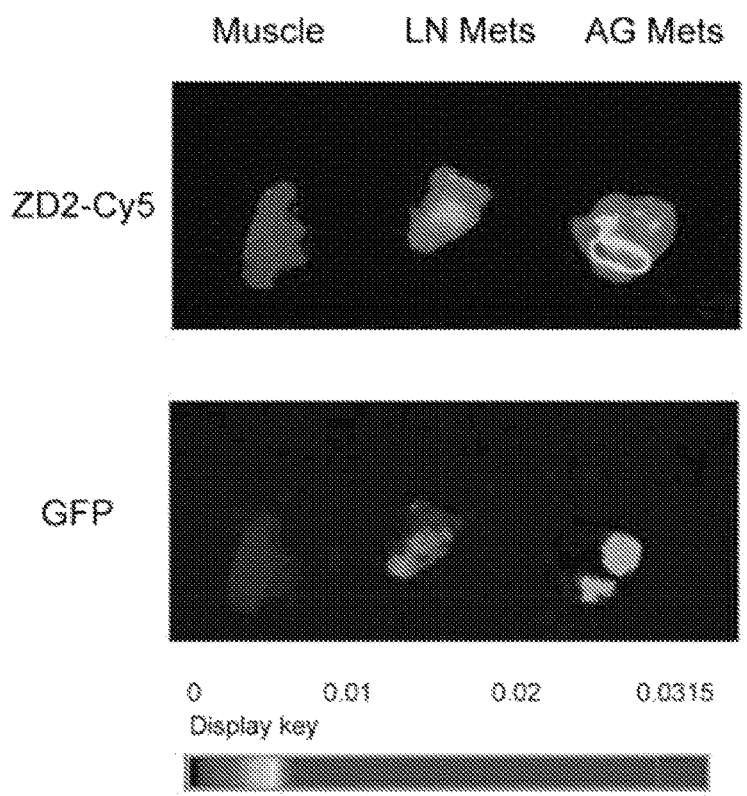
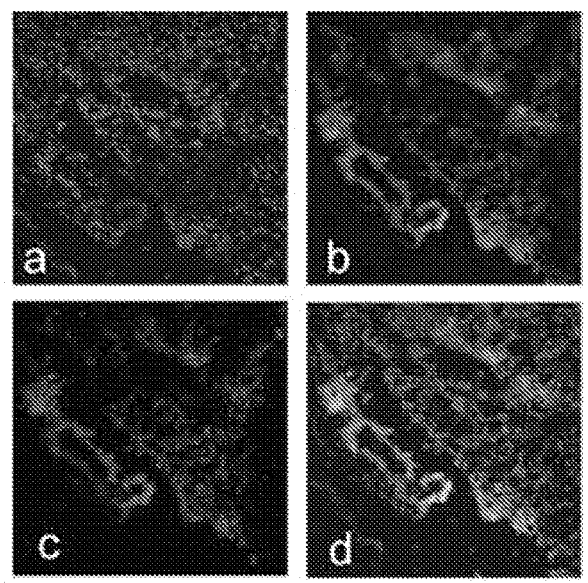
Figs. 8B-C

B.
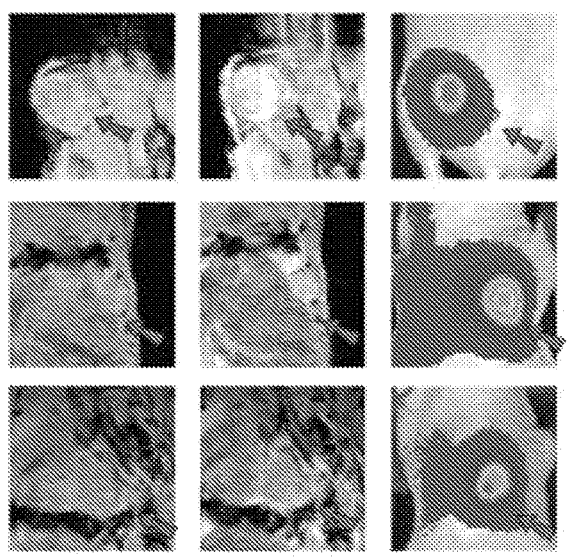
C.
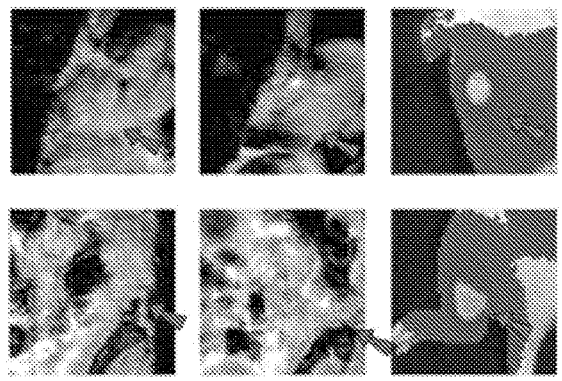
Figs. 9B-C

TARGETING PEPTIDES AND METHODS OF USE

RELATED APPLICATION

This application claims priority from U.S. Provisional Application No. 62/032,945, filed Aug. 4, 2014, the subject matter of which is incorporated herein by reference in its entirety.

GOVERNMENT FUNDING

This invention was made with government support under Grant No. EB000489, awarded by The National Institutes of Health. The United States government has certain rights to the invention.

BACKGROUND

Cancer detection and treatment are hindered by the inability to differentiate between cancer cells and normal cells. Better detection tools for cancer or tumor imaging are needed for earlier diagnosis of cancers. Molecular recognition of tumor cells would facilitate guided surgical resection. In order to improve surgical resection, targeted imaging tools must specifically label tumor cells, not only in the main tumor but also along the edge of the tumor and in the small tumor cell clusters that disperse throughout the body. Targeted imaging tools designed to label molecules that accumulate in the tumor microenvironment may also be advantageous as therapeutic targeting agents, as they can identify both the main tumor cell population and areas with infiltrating cells that contribute to tumor recurrence. The ability to directly target the tumor cell and/or its microenvironment would increase both the specificity and sensitivity of current treatments, therefore reducing non-specific side effects of chemotherapeutics that affect cells throughout the body.

SUMMARY

Embodiments described herein relate to targeting peptides that can specifically bind to EDB-FN or EDA-FN. The targeting peptides can be coupled to a detectable moiety to form a molecular probe. The molecular probe can be used to detect the location and/or distribution of cancer cells in tissue of a subject, the aggressiveness of cancer in a subject, and/or the efficacy of a cancer therapeutic and/or cancer therapy administered to a subject in need thereof.

In some embodiments, the targeting peptide can be selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.

In other embodiments, the detectable moiety can include an imaging agent and the molecular probe can be detectable upon administration to a subject by at least one of gamma imaging, positron emission tomography (PET) imaging, computer tomography (CT) imaging, magnetic resonance imaging, near infrared imaging, or fluorescent imaging. The detectable moiety can be, for example, at least one of an optical dye, MRI contrast agent, a PET agent, a SPECT agent, a CT contrast agent, radiolabel, or an ultrasound contrast agent.

In some embodiments, the targeting peptide can be covalently linked to the detectable moiety by a linker. The linker can be, for example, a peptide linker or polymer linker.

In still other embodiments, the molecular probe can be administered systematically to the subject to detect the distribution and/or location of cancer in the subject as well as the cancer aggressiveness. The cancer can include, for example, at least one of breast cancer, liver cancer, stomach cancer, colon cancer, pancreatic cancer, ovarian cancer, lung cancer, kidney cancer, prostate cancer, testicular cancer, glioblastoma, sarcoma, bone cancer, brain cancer, head and neck cancers, or skin cancer.

BRIEF DESCRIPTION OF THE DRAWINGS

FIGS. 1(A-D) illustrate: (A) A schematic drawing showing the construction of EDB expressing plasmid. DNA encoding EDB fragment was inserted under the control of T7 promoter, with infusion of 10×His tags on the N-terminal. Lac operator (lacO) allows control of EDB expression with IPTG induction. B) SDS-PAGE of lysates from EDB expressing E. coli. Lanes were labeled as follows: M: protein ladder; 1, E. coli cell lysate before induction with IPTG; 2, 1.5 h post induction; 3, 3 h post induction; 4, purified EDB solution from lysate acquired 3 hours after induction). C) MALDI-TOF mass spectrum of ZD2 peptide with the sequence of CTVRTSADC, [m/z M+]=954.23 (observed), 954.39 (calculated). D) Peptide ELISA for quantification of binding affinity between ZD2 and EDB protein.

FIGS. 2(A-D) illustrate: A) Morphology of PC3 cells with and without TGFβ1 induction. Images were taken by phage-contrast microscopy at 10× and 40× (insert). B) RT-PCR analysis of EDA, EDB, E-Cad, and N-Cad expression in cells after TGFβ1 induction relative to those without induction. C) Representative images of ZD2-Cy5 binding to cell periphery when TGFβ1 inducted PC3 cells were growing in growth medium containing 0.25 μM of ZD2-Cy5. Non-inducted cells were used as a control. Images were taken with confocal fluorescence microscopy at 40× and 100× (insert). D) Comparison of live cell staining between ZD2-Cy5 and free Cy5 dye (100× magnification).

FIGS. 3(A-D) illustrate: A) Representative fluorescence images of PC3 bearing mouse at 1.5 h after intravenous injection of 10 nmol ZD2-Cy5 or non-specific control CERAK-Cy5 (Cy5, left panel; GFP; right panel; white arrows point to tumors). B) Fluorescence intensity ratio between tumor and normal tissues (T/N ratio) as a function of time from mice injected with ZD2-Cy5 or CERAK-Cy5 (N=3). C) Representative fluorescence images of organs harvested from PC3-GFP tumor bearing mouse 5 h post-injection with ZD2-Cy5 or CERAK-Cy5. Cy5 channel (left), GFP channel (middle), and bright field images (right) were shown. Organs are represented with numbers: 1, tumor; 2, liver; 3, muscle; 4, heart; 5, brain; 6, lung; 7, spleen. D) Western blot analysis of tumor, liver, and lung lysates harvested from PC3 tumor bearing mouse.

FIGS. 4(A-C) illustrate A) Representative fluorescence images of tumor sections from PC3 tumor model injected with ZD2-Cy5 or CERAK-Cy5. B) Representative fluorescence images of the liver and lung sections from the same mice. Scale bar: 20 μm. C) Correlation of ZD2 distribution with EDB-FN (BC-1) distribution and blood vessel distribution (anti-CD31) in PC3 tumor sections. Scale bar: 20 μm.

FIGS. 5(A-E) illustrate: A) H&E staining, immunofluorescence staining with BC-1, and ZD2-Cy5 staining of human prostate BPH section and prostate tumor sections of GS7 (3+4) and GS9 (4+5). Scale bar: 100 µm. B) Representative Cy5 histograms indicate distribution of Cy5 pixel intensities in images shown in A. Labeled portion of the histograms is the percent pixel counts of Cy5 pixel value ranging from 50 to 255 (upper panel). Analysis of histogram distribution in each prostate section of different Gleason scores was also shown. Box chart represents distribution of data acquired in the histogram analysis (lower panel). C) The image of a region of GS7 prostate that contains both high staining glandular areas and low staining areas, showing the relationship between staining level and gland morphology. Low staining glands were labeled with white arrows and high staining glands are labeled with arrowheads. Image was acquired with Olympus Virtual Slide Microscopy system. Scale bar: 40 µm. D) Western blot analysis of prostate lysates from normal or cancerous prostate tissues GS7 (3+4). EDB-FN expression was determined by BC-1, β-actin expression was used as loading control. Column graph indicates difference in levels of expression of EDB-FN indicated by western blot (n=3; ***, p<0.001). E) Competitive staining with BC-1 (green) and ZD2 (red). BC-1 binding blocked the binding of ZD2-Cy5. Scale bar: 100 µm.

FIGS. 6(A-B) illustrate: A) A graph showing relative mRNA expression of EDB FN in 4T1 cell line with TGFβ compared with non-induced cells (control). B) Western blot analysis of EDB FN expression in tumor tissues collected from different organs. β-actin was used as a loading control.

DETAILED DESCRIPTION

Figure 7A:
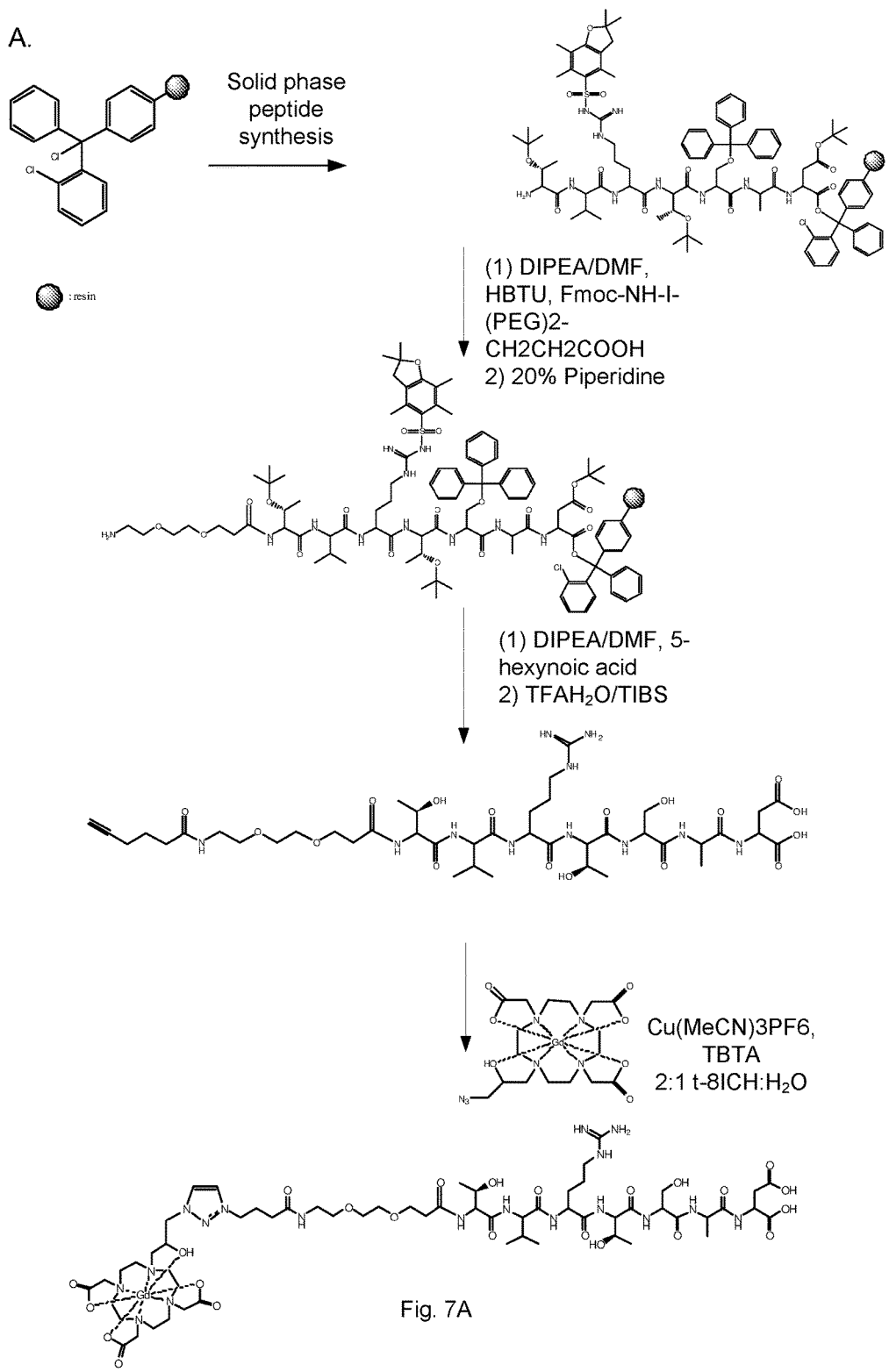
FIGS. 7(A-C) illustrate: A) A synthesis method of l-ZD2-Gd(HP-DO3A). B) Maldi-Tof mass spectrum of l-ZD2-Gd (HP-DO3A). C) Measurement of relaxivities ($T_1$ and $T_2$) of l-ZD2-Gd(HP-DO3A).

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

The term "agent" is used herein to denote a chemical compound, a mixture of chemical compounds, a biological macromolecule, or an extract made from biological materials.

The terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

The terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

The term "chimeric protein" or "fusion protein" is a fusion of a first amino acid sequence encoding a polypeptide with a second amino acid sequence defining a domain (e.g. polypeptide portion) foreign to and not substantially homologous with any domain of the first polypeptide. A chimeric protein may present a foreign domain, which is found (albeit in a different protein) in an organism, which also expresses the first protein, or it may be an "interspecies", "intergenic", etc. fusion of protein structures expressed by different kinds of organisms.

The term "isolated" as used herein with respect to nucleic acids, such as DNA or RNA, or amino acids refers to molecules separated from other DNAs, or RNAs, polypeptides or protein respectively, which are present in the natural source of the macromolecule. The term isolated as used herein also refers to a nucleic acid or peptide that is substantially free of cellular material, or culture medium when produced by recombinant DNA techniques, or chemical precursors or other chemicals when chemically synthesized. Moreover, an "isolated nucleic acid" or "isolated peptide" is meant to include nucleic acid fragments or peptide fragments, which are not naturally occurring as fragments and would not be found in the natural state.

The term "mutant" refers to any change in the genetic material of an organism, in particular a change (i.e., deletion, substitution, addition, or alteration) in a wild type polynucleotide sequence or any change in a wild type protein. The term "variant" is used interchangeably with "mutant". Although it is often assumed that a change in the genetic material results in a change of the function of the protein, the terms "mutant" and "variant" refer to a change in the sequence of a wild type protein regardless of whether that change alters the function of the protein (e.g., increases, decreases, imparts a new function), or whether that change has no effect on the function of the protein (e.g., the mutation or variation is silent).

The term "nucleic acid" refers to polynucleotides, such as deoxyribonucleic acid (DNA), and, where appropriate, ribonucleic acid (RNA). The term should also be understood to include, as equivalents, analogs of RNA or DNA made from nucleotide analogs, and, as applicable to the embodiment being described, single (sense or antisense) and double-stranded polynucleotides.

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The terms "patient", "subject", "mammalian host," and the like are used interchangeably herein, and refer to mammals, including human and veterinary subjects.

The terms "peptide(s)", "protein(s)" and "polypeptide(s)" are used interchangeably herein. As used herein, "polypeptide" refers to any peptide or protein comprising two or more amino acids joined to each other by peptide bonds or modified peptide bonds (i.e., peptide isomers). "Polypeptide(s)" refers to both short chains, commonly referred as peptides, oligopeptides or oligomers, and to longer chains generally referred to as proteins.

The terms "polynucleotide sequence" and "nucleotide sequence" are also used interchangeably herein.

"Recombinant," as used herein, means that a protein is derived from a prokaryotic or eukaryotic expression system.

The phrases "systemic administration," "administered systemically," "peripheral administration" and "administered peripherally" as used herein mean the administration of a compound, agent or other material other than directly into a specific tissue, organ, or region of the subject being treated (e.g., brain), such that it enters the animal's system and, thus, is subject to metabolism and other like processes, for example, subcutaneous administration.

The term "wild type" refers to the naturally-occurring polynucleotide sequence encoding a protein, or a portion thereof, or protein sequence, or portion thereof, respectively, as it normally exists in vivo.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

Embodiments described herein relate to targeting peptides for use in detecting, monitoring, and/or imaging cancer cell distribution and/or location and/or cancer cell metastasis, migration, and/or invasion in a subject, detecting and/or monitoring cancer cell aggressiveness and/or malignancy in a subject, and/or determining and/or monitoring the efficacy of a cancer therapeutic and/or cancer therapy administered to a subject in need thereof.

The targeting peptides described herein include a peptide sequence that specifically binds to and/or complexes with oncofetal fibronectin (onfFN) isoforms, extradomain-B fibronectin (EDB-FN) or extradomain-A (EDA-FN) fibronectin. Cancer, and particularly, malignant cancer has a unique tumor microenvironment that facilitates cancer cell survival, proliferation, and metastasis. The presence of onfFN has been shown in various human cancer types, including prostate and breast cancer. High expression of onfFN, EDB-FN and/or EDA-FN, inversely correlated with cancer aggressiveness and patient survival. It was found that contrast agents or molecular probes that include target peptides, which specifically bind to EDB-FN and/or EDB-FN, can be used for detecting, monitoring, and/or imaging cancer cells in tissue of a subject as well as to determine cancer cell aggressiveness, malignancy, metastasis, migration, dispersal, and/or invasion.

Molecular probes including the targeting peptides can be administered systemically to a subject, such as by intravenous or parenteral administration, and readily target the extracellular matrix proteins EDB-FN and/or EDA-FN to define cancer cell location, distribution, and/or aggressiveness as well as tumor cell margins in the subject.

In some embodiments, the targeting peptide can specifically bind to EDB-FN. Targeting peptides that specifically bind EDB-FN can include linear peptides having the amino acid sequences of TVRTSAD (SEQ ID NO: 1), NWGDRIL (SEQ ID NO: 2), NWGKPIK (SEQ ID NO: 3), SGVKSAF (SEQ ID NO: 4), GVKSYNE (SEQ ID NO: 5), IGKTNTL (SEQ ID NO: 6), IGNSNTL (SEQ ID NO: 7), IGNTIPV (SEQ ID NO: 8), and LYANSPF (SEQ ID NO: 9) or cyclic peptides having the amino acid sequences of CTVRTSADC (SEQ ID NO: 10), CNWGDRILC (SEQ ID NO: 11), CNWGKPIKC (SEQ ID NO: 12), CSGVKSAFC (SEQ ID NO: 13), CGVKSYNEC (SEQ ID NO: 14), CIGKTNTLC (SEQ ID NO: 15), CIGNSNTLC (SEQ ID NO: 16), CIGNTIPVC (SEQ ID NO: 17), or CLYANSPFC (SEQ ID NO: 18). In other embodiments, the targeting peptide can specifically bind to EDA-FN. Targeting peptides that specifically bind EDA-FN can include linear peptides having the amino acid sequences of WNYPFRL (SEQ ID NO: 19), SNTSYVN (SEQ ID NO: 20), SFSYTSG (SEQ ID NO: 21), WSPAPMS (SEQ ID NO: 22), TREHPAQ (SEQ ID NO: 23), or ARIIDNA (SEQ ID NO: 24) or cyclic peptides having the amino acid sequences of CWNYPFRLC (SEQ ID NO: 25), CSNTSYVNC (SEQ ID NO: 26), CSFSYTSGC (SEQ ID NO: 27), CWSPAPMSC (SEQ ID NO: 28), CTREHPAQC (SEQ ID NO: 29), or CARIIDNAC (SEQ ID NO: 30).

The targeting peptides can be subject to various changes, substitutions, insertions, and deletions where such changes provide for certain advantages in its use. In this regard, targeting peptides that bind to and/or complex with EDB-FN and/or EDA-FN can be substantially homologous with, rather than be identical to, the sequence of a recited peptide where one or more changes are made and it retains the ability to function as specifically binding to and/or complexing with EDB-FN and/or EDA-FN.

The targeting peptides can be in any of a variety of forms of polypeptide derivatives, that include amides, conjugates with proteins, cyclized polypeptides, polymerized polypeptides, analogs, fragments, chemically modified polypeptides, and the like derivatives.

The term "analog" includes any peptide having an amino acid residue sequence substantially identical to a sequence specifically shown herein in which one or more residues have been conservatively substituted with a functionally similar residue and that specifically binds to and/or complexes with EDB-FN and/or EDA-FN as described herein. Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such peptide displays the requisite binding activity.

"Chemical derivative" refers to a subject peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-benzylhistidine. Also included as chemical derivatives are those polypeptides, which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Peptides described herein also include any peptide having one or more additions and/or deletions or residues relative to the sequence of a peptide whose sequence is shown herein, so long as the requisite binding specificity or activity is maintained.

The term "fragment" refers to any subject peptide having an amino acid residue sequence shorter than that of a polypeptide whose amino acid residue sequence is shown herein.

The targeting peptides can be synthesized by any of the techniques that are known to those skilled in the polypeptide art, including recombinant DNA techniques. Synthetic chemistry techniques, such as a solid-phase Merrifield-type synthesis, can be used for reasons of purity, antigenic specificity, freedom from undesired side products, ease of production and the like. A summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, Adv. Enzymol., 32:221-96, 1969; Fields et al., in J. Peptide Protein Res., 35:161-214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as an example, the protected or derivatized amino acid can be attached to an inert solid support through its unprotected carboxyl or amino group. The protecting group of the amino or carboxyl group can then be selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group can then be removed from this newly added amino acid residue, and the next amino acid (suitably protected) is then added, and so forth. After all the desired amino acids have been linked in the proper sequence, any remaining terminal and side group protecting groups (and solid support) can be removed sequentially or concurrently, to afford the final linear polypeptide.

Furthermore, the targeting peptides described herein can be used as a starting point to develop higher affinity small molecules, peptides, antibodies, and/or antibody fragments with similar ligand binding capabilities. The development and screening of small molecules from pharmacophores of the peptides using, for example, in silico screening, can be readily performed, and the binding affinity of such identified molecules can be readily screened against targeting peptides using assays described herein to select small molecule agents.

Additional residues may also be added at either terminus of a peptide for the purpose of providing a "linker" by which the peptides can be conveniently linked and/or affixed to other polypeptides, proteins, detectable moieties, labels, solid matrices, or carriers.

Amino acid residue linkers are usually at least one residue and can be 40 or more residues, more often 1 to 10 residues. Typical amino acid residues used for linking are glycine, tyrosine, cysteine, lysine, glutamic and aspartic acid, or the like. In addition, a subject targeting peptide agent can differ by the sequence being modified by terminal-$NH_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

In some embodiments, the linker can be a flexible peptide linker that links the targeting peptide to other polypeptides, proteins, and/or molecules, such as detectable moieties, labels, solid matrices, or carriers. A flexible peptide linker can be about 20 or fewer amino acids in length. For example, a peptide linker can contain about 12 or fewer amino acid residues, e.g., 1, 2, 3, 4, 5, 6, 7, 8, 9, 10, 11, and 12. In some cases, a peptide linker comprises two or more of the following amino acids: glycine, serine, alanine, and threonine.

Alternatively, a linking molecule may be a non-peptide linker. As used herein, a non-peptide linker useful for the compounds described herein is a biocompatible polymer including two or more repeating units linked to each other. Examples of the non-peptide polymer include but are not limited to: polyethylene glycol (PEG), polypropylene glycol (PPG), co-poly (ethylene/propylene) glycol, polyoxyethylene (POE), polyurethane, polyphosphazene, polysaccharides, dextran, polyvinyl alcohol, polyvinylpyrrolidones, polyvinyl ethyl ether, polyacryl amide, polyacrylate, polycyanoacrylates, lipid polymers, chitins, hyaluronic acid, and heparin. For more detailed descriptions of non-peptide linkers, see, for example, WO/2006/107124, which is incorporated by reference herein. Typically such linkers will have a range of molecular weight of from about 1 kDa to 50 kDa, depending upon a particular linker. For example, a typical PEG has a molecular weight of about 1 to 5 kDa, and polyethylene glycol has a molecular weight of about 5 kDa to 50 kDa, and more preferably about 10 kDa to 40 kDa.

In some embodiments, the targeting peptides can be directly or indirectly labeled with a detectable moiety to form a targeted molecular probe or contrast agent. The role of a detectable moiety is to facilitate the detection step of a detection or diagnostic method by allowing visualization of the complex formed by binding of a molecular probe comprising a targeting peptide to EDB-FN and/or EDA-FN. The detectable moiety can be selected such that it generates a signal, which can be measured and whose intensity is related (preferably proportional) to the amount of the molecular probe bound to the tissue being analyzed. Methods for labeling biological molecules, such as peptides, are well-known in the art.

Any of a wide variety of detectable moieties can be used with the targeting peptides described herein. Examples of detectable moieties include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In some embodiments, the molecular probes described herein may be used in conjunction with non-invasive imaging techniques for in vivo imaging of the molecular probe, such as magnetic resonance spectroscopy (MRS) or imaging (MRI), or gamma imaging, such as positron emission tomography (PET), single-photon emission computed tomography (SPECT), CT contrast image, or ultrasound imaging. The term "in vivo imaging" refers to any method, which permits the detection of a labeled targeting peptide, as described above. For gamma imaging, the radiation emitted from the organ or area being examined is measured and expressed either as total binding or as a ratio in which total binding in one tissue is normalized to (for example, divided by) the total binding in another tissue of the same subject during the same in vivo imaging procedure. Total binding in vivo is defined as the entire signal detected in a tissue by an in vivo imaging technique without the need for correction by a second injection of an identical quantity of molecular probe along with a large excess of unlabeled, but otherwise chemically identical compound.

In one example, the detectable moiety can include a radiolabel, that is coupled (e.g., attached or complexed) with the targeting peptides using general organic chemistry techniques. Radiolabels, such as $^{123}I$, $^{131}I$, $^{125}I$, $^{18}F$, $^{11}C$, $^{75}Br$, $^{76}Br$, $^{124}I$, $^{13}N$, $^{64}Cu$, $^{32}P$, $^{35}S$, can be used for PET techniques imaging by well known in the art and are described by Fowler, J. and Wolf, A. in POSITRON EMISSION TOMOGRAPHY AND AUTORADIOGRAPHY (Phelps, M., Mazziota, J., and Schelbert, H. eds.) 391-450 (Raven Press, N Y 1986) the contents of which are hereby incorporated by reference. The detectable moiety can also include $^{123}I$ for SPECT. The $^{123}I$ can be coupled to the targeting peptide by any of several techniques known to the art. See, e.g., Kulkarni, Int. J. Rad. Appl. & Inst. (Part B) 18: 647 (1991), the contents of which are hereby incorporated by reference. In addition, the detectable moiety can include any radioactive iodine isotope, such as, but not limited to $^{131}I$, $^{125}I$, or $^{123}I$. The radioactive iodine isotopes can be coupled to the targeting peptide by iodination of a diazotized amino derivative directly via a diazonium iodide, see Greenbaum, F. Am. J. Pharm. 108: 17 (1936), or by conversion of the unstable diazotized amine to the stable triazene, or by conversion of a non-radioactive halogenated precursor to a stable tri-alkyl tin derivative, which then can be converted to the iodo compound by several methods well known to the art.

For purposes of in vivo imaging, the type of detection instrument available is a major factor in selecting a given detectable moiety. For instance, the type of instrument used will guide the selection of a stable isotope. The half-life should be long enough so that it is still detectable at the time of maximum uptake by the target, but short enough so that the host does not sustain deleterious effects.

Figure 11:
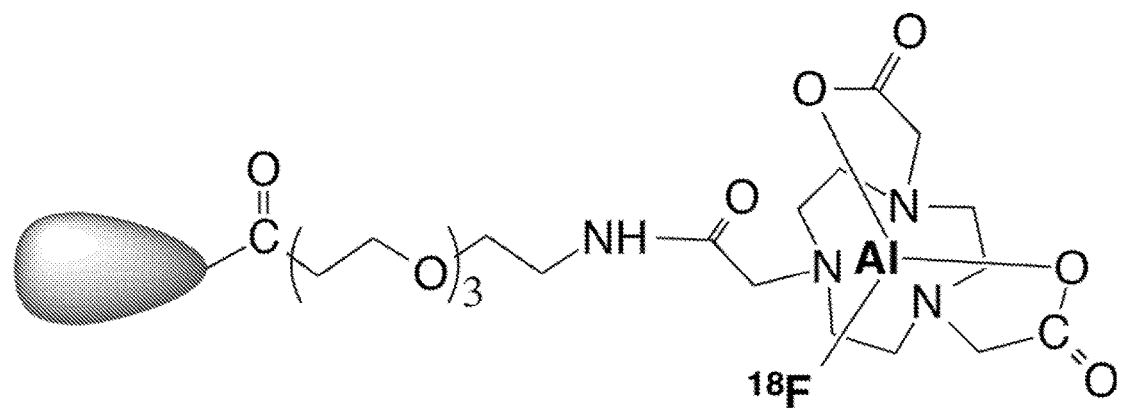
FIG. 11 is a schematic illustration of a molecular probe in accordance with an embodiment of the application.

The detectable moiety can further include known metal radiolabels, such as Technetium-99m ($^{99m}Tc$), $^{153}Gd$, $^{111}In$, $^{67}Ga$, $^{201}Tl$, $^{68}Ga$, $^{82}Rb$, $^{64}Cu$, $^{90}Y$, $^{188}Rh$, T(tritium), $^{153}Sm$, $^{89}$Sr, and $^{211}$At as well as $^{18}$F modified metal radiolabels for PET imaging. For example, the 18F modified radiolabel can have the structure shown in FIG. 11, wherein the targeting peptide is coupled to the radiolabel. Modification of the targeting peptides to introduce ligands that bind such metal ions can be effected without undue experimentation by one of ordinary skill in the radiolabeling art. The metal radiolabeled molecular probes can then be used to detect cancers, such as prostate cancer in the subject. Preparing radiolabeled derivatives of Tc99m is well known in the art. See, for example, Zhuang et al., "Neutral and stereospecific Tc-99m complexes: [99mTc]N-benzyl-3,4-di-(N-2-mercaptoethyl)-amino-pyrrolidines (P-BAT)" Nuclear Medicine & Biology 26(2):217-24, (1999); Oya et al., "Small and neutral Tc(v)O BAT, bisaminoethanethiol (N2S2) complexes for developing new brain imaging agents" Nuclear Medicine & Biology 25(2):135-40, (1998); and Hom et al., "Technetium-99m-labeled receptor-specific small-molecule radiopharmaceuticals: recent developments and encouraging results" Nuclear Medicine & Biology 24(6):485-98, (1997).

Fluorescent labeling agents or infrared agents include those known in the art, many of which are commonly commercially available, for example, fluorophores, such as ALEXA 350, PACIFIC BLUE, MARINA BLUE, ACRIDINE, EDANS, COUMARIN, BODIPY 493/503, CY2, BODIPY Fla.-X, DANSYL, ALEXA 488, FAM, OREGON GREEN, RHODAMINE GREEN-X, TET, ALEXA 430, CAL GOLD.™., BODIPY R6G-X, JOE, ALEXA 532, VIC, HEX, CAL ORANGE.™., ALEXA 555, BODIPY 564/570, BODIPY TMR-X, QUASAR.™. 570, ALEXA 546, TAMRA, RHODAMINE RED-X, BODIPY 581/591, CY3.5, ROX, ALEXA 568, CAL RED, BODIPY TR-X, ALEXA 594, BODIPY 630/650-X, PULSAR 650, BODIPY 630/665-X, ALEXA 647, IR800, and QUASAR 670. Fluorescent labeling agents can include other known fluorophores, or proteins known in the art, for example, green fluorescent protein. The disclosed targeting peptides can be coupled to the fluorescent labeling agents, administered to a subject or a sample, and the subject/sample examined by fluorescence spectroscopy or imaging to detect the labeled compound.

Quantum dots, e.g., semiconductor particles, can be employed as described in Gao, et al "In vivo cancer targeting and imaging with semiconductor quantum dots", Nature Biotechnology, 22, (8), 2004, 969-976, the entire teachings of which are incorporated herein by reference. The disclosed targeting peptides can be coupled to the quantum dots, administered to a subject or a sample, and the subject/sample examined by fluorescence spectroscopy or imaging to detect the labeled compound.

Numerous magnetic resonance imaging (MRI) contrast agents are known in the art, for example, positive contrast agents and negative contrast agents. The disclosed targeting peptides can be coupled to the MRI agents, administered to a subject or a sample, and the subject/sample examined by MRI or imaging to detect the labeled compound. Positive contrast agents (typically appearing predominantly bright on MRI) can include typically small molecular weight organic compounds that chelate or contain an active element having unpaired outer shell electron spins, e.g., gadolinium, manganese, iron oxide, or the like. Typical contrast agents include gadolinium(III)chelates, such as gadopentetate dimeglumine, gadoteridol, gadoterate meglumine, mangafodipir trisodium, gadodiamide, and others known to the art. Negative contrast agents (typically appearing predominantly dark on MRI) can include small particulate aggregates comprised of superparamagnetic materials, for example, particles of superparamagnetic iron oxide (SPIO). Negative contrast agents can also include compounds that lack the hydrogen atoms associated with the signal in MRI imaging, for example, perfluorocarbons (perfluorochemicals).

In certain aspects, the detectable moiety includes a chelating agent and a metal ion. The chelating agent generally possesses one or more groups capable of forming a covalent bond with the peptide. A number of different chelating agents known in the art can be used herein. In one aspect, the chelating agent comprises an acyclic or cyclic compound comprising at least one heteroatom (e.g., oxygen, nitrogen, sulfur, phosphorous) that has lone-pair electrons capable of coordinating with the imaging agent. An example of an acyclic chelating agent includes ethylenediamine. Examples of cyclic chelating agents include diethylenetriaminepentaacetate (DTPA) or its derivatives, 1,4,7,10-tetraazadodecanetetraacetate (DOTA) and its derivatives, 1,4,7,10-tetraazadodecane-1,4,7-triacetate (DO3A) and its derivatives, ethylenediaminetetraacetate (EDTA) and its derivatives, 1,4,7,10-tetraazacyclotridecanetetraacetic acid (TRITA) and its derivatives, 1,4,8,11-tetraazacyclotetradecane-1,4,8,11-tetraacetic acid (TETA) and its derivatives, 1,4,7,10-tetraazadodecanetetramethylacetate (DOTMA) and its derivatives, 1,4,7, 10-tetraazadodecane-1,4,7-trimethylacetate (DO3MA) and its derivatives, N,N',N''', N''''-tetraphosphonatomethyl-1,4,7,10-tetraazacyclododecane (DOTP) and its derivatives, 1,4,7,10-tetraazacyclododecane-1,4,7,10-tetrakis(methylene methylphosphonic acid) (DOTMP) and its derivatives, 1,4,7,10-tetraazacyclododecane-1,4,7,10-tetrakis(methylene phenylphosphonic acid) (DOTPP) and its derivatives, or N,N'-ethylenedi-L-cysteine or its derivatives. The term "derivative" is defined herein as the corresponding salt and ester thereof of the chelating agent.

The selection of the metal ion can vary depending upon the detection technique (e.g., MRI, PET, etc.). In one aspect, metal ions useful in magnetic resonance imaging include $Gd^{+3}$, $Eu^{+3}$, $Tm^{+3}$, $Dy^{+3}$, $Yb^{+3}$, $Mn^{+2}$, or $Fe^{+3}$ ions. In another aspect, ions useful in PET and SPECT imaging include $^{55}$Co, $^{64}$Cu, $^{67}$Cu, $^{47}$Sc, $^{66}$Ga, $^{68}$Ga, $^{90}$Y, $^{97}$Ru, $^{99m}$Tc, $^{111}$h, $^{109}$Pd, $^{153}$Sm, $^{177}$Lu, $^{186}$Re, $^{188}$Re. In another aspect, the imaging agent comprises an MRI agent, wherein the MRI agent comprises a chelating agent and a metal ion comprising $Gd^{+3}$, $Eu^{+3}$, $Tm^{+3}$, $Dy^{+3}$, $Yb^{+3}$, $Mn^{+2}$, or $Fe^{+3}$ ions.

In some embodiments, the targeting peptide can be coupled to the detectable moiety using a linking molecule. The linking molecule may be a peptide linker. Alternatively, a linking molecule may be a non-peptide linker, such as a polymer or monomer linker.

In still other embodiments, the targeting peptide can be coupled to a Fc region of an IgG to form a targeting peptide-Fc chimera that can specifically bind to EDB-FN and/or EDA-FN. Advantageously, the targeting peptide-Fc chimera can induce immune responses, such as complement-dependent lysis and antibody-dependent cellular cytotoxicity, that target tumor cells thereby eliciting anti-tumor activities.

Chimeric proteins that can combine the Fc regions of IgG with one or more domains of another protein, such as various cytokines and soluble receptors, are known. These chimeric proteins can be fusions of human Fc regions and human domains of another protein. These chimeric proteins would then be a "humanized Fc chimera". See, for example, Capon et al., Nature, 337:525-531, 1989; Chamow et al., Trends Biotechnol., 14:52-60, 1996); U.S. Pat. Nos. 5,116, 964 and 5,541,087. The chimeric protein can be a homodimeric protein linked through cysteine residues in the hinge region of IgG Fc, resulting in a molecule similar to an IgG molecule without the $C_{H1}$ domains and light chains. Due to the structural homology, such Fc fusion proteins exhibit in vivo pharmacokinetic profile comparable to that of human IgG with a similar isotype. This approach has been applied to several therapeutically important cytokines, such as IL-2 and IFN-α, and soluble receptors, such as TNF-Rc and IL-5-Rc (See, for example, U.S. Pat. Nos. 5,349,053, 6,224,867 and 7,250,493).

In some embodiments, the targeting peptide-Fc chimera is a chimeric molecule that includes a human sequence encoded targeting peptide described herein fused to a human Fc fragment and is capable of binding to or complexing with EDB-FN and/or EDA-FN that is expressed by a cancer cell or another cell in the cancer cell microenvironment.

The targeting peptide portion of the polypeptide-Fc chimera, similar to the targeting peptides described above, can be subject to various changes, substitutions, insertions, and deletions where such changes provide for certain advantages in its use. In this regard, the target peptide portion can correspond to or be substantially homologous with, rather than be identical to, the sequence of a recited targeting peptide where one or more changes are made and it retains the ability to function as specifically binding to and/or complexing with the proteolytically cleaved extracellular portion of an Ig superfamily cell adhesion molecule.

The Fc portion of the targeting peptide-Fc chimera is a domain that binds an activating Fc receptor, such as an activating Fc Ig domain and includes the hinge region that allows for dimerization. The Fc portion of the targeting peptide-Fc chimera can be readily adapted to render it species-specific. For use in a murine system, e.g., cells derived from a mouse, the Fc fragment used to generate the targeting peptide-Fc can be that of a murine origin. In some embodiments, an Fc fragment of the murine IgG2a can be used.

For use in a human subject, e.g., for cancer treatment, the Fc fragment used to generate the targeting peptide-Fc chimera is of a human origin. In some embodiments, the targeting peptide-Fc chimera comprises an activating Fc Ig domain. Among the four human IgG isotypes, an activating Fc domain of $IgG_1$ can be used for the preparation of the polypeptide-Fc chimera.

It is appreciated that different antibody isotypes have a varying degree of cytotoxic potential in vivo (See, for example, Nimmerjahn F. & Ravetch J V., 2006, Immunity, 24:19-28). For example, the murine IgG2a and IgG2b isotypes are more efficient in clearing infections, such as bacterial infections and viral infections and in killing tumor cells than their $IgG_1$ or $IgG_3$ counterparts. This is attributable at least in part to differential ratios of activating versus inhibitory FcRs present in vivo. Similarly, with respect to human IgG isotypes, $IgG_1$ and $IgG_3$ have a stronger interaction with FcRs than $IgG_2$ or $IgG_4$. Moreover, certain polymorphic allotypes of a given isotype may influence affinity for an Fc receptor. Indeed, there are allelic variants of activating FcRs that will significantly affect the affinity for certain antibody isotypes. For example, the FcγRIIIa receptor 158V allotype displays a higher affinity for human immunoglobulin $G_1$ and increased antibody-dependent cellular cytotoxicity (Cartron G. et al., 2002, Blood, 99: 754-758).

Thus, as shall be clear to the skilled artisan, it is possible to optimize the interaction between the Fc portion of the targeting peptide-Fc chimera to its corresponding Fc receptor by strategically selecting or modifying the Fc allele used for preparing the polypeptide-Fc chimera. Accordingly, a mutant or an allotype of an Fc fragment can be used here for the polypeptide-Fc chimera described herein. A number of useful mutations within an Fc domain have been described, which can affect the interaction of an Fc and its receptor, the effector function of the Fc, as well as the half-life of the Fc-containing molecule. These include specific amino acid substitutions and/or modifications to carbohydrate moieties in the Fc. For review, see, for example, Liu et al., 2008, Immunological Reviews, 222:9-27; Nimmerjahn & Ravetch, 2007, Curr. Opin. Immunol., 19(2): 239-45.

In other embodiments, the targeting peptide-Fc chimera can be engineered with an enhanced complement activity. Generally, complement can be activated by at least three pathways, leading to the formation of the membrane attack complex (MAC) C5b-9, which forms pores in the plasma membranes of target cells and causes their lysis. C1q binding to the Fc domain is a critical step in this process. Among the human IgG subclasses, only IgG1 and IgG3 can initiate the complement cascade. In some embodiments, mutations are introduced to the Fc domain of the polypeptide-Fc chimera, so as to promote C1q recruitment and the C1q-Fc interaction. The residues of the Fc targeted for such mutations include, but are not limited to: Asp270, Lys322, Pro329 and Pro331. These mutations involve substituting the corresponding residue(s) with nonpolar neutral amino acids, such as Ala, Met, or Trp. In a specific embodiment, the polypeptide-Fc contains the mutation, Lys326Trp, Glu333Ser or both.

In addition, it should be noted that when chimeric or fusion proteins with artificial sequences and activities are used for diagnostic applications, in some circumstances, patients administered such a chimeric or fusion protein trigger an unwanted immune response, such as development of antibodies against the agent. Certain structural modifications of an Fc fragment have been shown to reduce immunogenicity of a therapeutic fusion protein. See, for example, U.S. Pat. No. 6,992,174 B2, which is incorporated by reference herein; Liu et al., 2008, Immunological Reviews, 222:9-27. Such modifications may be useful for an effective design of the targeting peptide-Fc chimera described herein.

The targeting peptide-Fc chimera used in the methods may include a linking moiety that connects the targeting peptide portion with an Fc fragment. In some cases, a hinge region of Fc fusion protein molecules serves as a spacer between the Fc region and the fused polypeptide (e.g., soluble receptor), allowing these two parts of the molecule to function separately.

In some embodiments, the Fc portion and the targeting peptide portion that comprise a chimeric molecule are linked via a linking molecule which is not a contiguous portion of either the polypeptide or Fc portions and which covalently joins an amino acid of the polypeptide to an amino acid of Fc. As used herein, a linking molecule that is "not a contiguous portion" means that the targeting peptide portion and the Fc portion of the chimera are connected via an additional element that is not a part of the polypeptide or immunoglobulin that is contiguous in nature with either of the chimeric portions and functions as a linker.

In some embodiments, the linking molecule may be a peptide linker. Where the linker is a peptide linker, the polypeptide-Fc chimera may be produced as a single recombinant polypeptide using a conventional molecular biological/recombinant DNA method.

Molecular biological and biochemical techniques for preparing an Fc chimera are known. In some embodiments, the targeting peptide-Fc chimera can be produced by conventional recombinatory DNA methods. In other embodiments, the targeting peptide-Fc chimera can be produced as a single (e.g., contiguous) recombinant polypeptide. In still other embodiments, two or more portions of the targeting peptide-Fc can be produced as separate fragments and are subsequently linked together to yield the targeting peptide-Fc chimera. For example, the polypeptide portion of the targeting peptide-Fc chimera and an Fc portion of the targeting peptide-Fc chimera can each be produced as separate recombinant polypeptides then fused together by a chemical linking means to yield the targeting peptide-Fc. This production methodology may be preferred particularly in situations where a non-peptide linking molecule is employed. Similarly, this production methodology may be also preferred if a chimeric targeting peptide-Fc does not fold correctly (e.g., does not properly bind a ligand) when made as a single contiguous polypeptide.

For the production of recombinant polypeptides, a variety of host organisms may be used. Examples of hosts include, but are not limited to: bacteria, such as E. coli, yeast cells, insect cells, plant cells and mammalian cells. Choice of a host organism will depend on the particular application of the targeting peptide-Fc chimera. The skilled artisan will understand how to take into consideration certain criteria in selecting a suitable host for producing the recombinant polypeptide. Factors affecting selection of a host include, for example, post-translational modifications, such as phosphorylation and glycosylation patterns, as well as technical factors, such as the general expected yield and the ease of purification. Host-specific post-translational modifications of the targeting peptide-Fc chimera, which is to be used in vivo, should be carefully considered because certain post-translational modifications are known to be highly immunogenic (antigenic).

The molecular probe comprising the targeting peptide described herein can be administered to the subject by, for example, systemic, topical, and/or parenteral methods of administration. These methods include, e.g., injection, infusion, deposition, implantation, or topical administration, or any other method of administration where access to the tissue by the molecular probe is desired. In one example, administration of the molecular probe can be by intravenous injection of the molecular probe in the subject. Single or multiple administrations of the probe can be given. "Administered", as used herein, means provision or delivery of a molecular probe in an amount(s) and for a period of time(s) effective to label cancer cells in the subject.

Molecular probes comprising the targeting peptides described herein can be administered to a subject in a detectable quantity of a pharmaceutical composition containing a molecular probe or a pharmaceutically acceptable water-soluble salt thereof, to a patient.

A "detectable quantity" means that the amount of the molecular probe that is administered is sufficient to enable detection of binding or complexing of the probe to EDB-FN and/or EDA-FN expressed by the cancer cells or other cells in the cancer cell microenvironment. An "imaging effective quantity" means that the amount of the molecular probe that is administered is sufficient to enable imaging of binding or complexing of the molecular probe to the EDB-FN and/or EDA-FN of the cancer cells or other cells in the cancer cell microenvironment.

Formulation of the molecular probe to be administered will vary according to the route of administration selected (e.g., solution, emulsion, capsule, and the like). Suitable pharmaceutically acceptable carriers may contain inert ingredients which do not unduly inhibit the biological activity of the compounds. The pharmaceutically acceptable carriers should be biocompatible, e.g., non-toxic, non-inflammatory, non-immunogenic and devoid of other undesired reactions upon the administration to a subject. Standard pharmaceutical formulation techniques can be employed, such as those described in Remington's Pharmaceutical Sciences, ibid. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. Formulation will vary according to the route of administration selected (e.g., solution, emulsion, capsule).

Any polypeptide or compound may also be used in the form of a pharmaceutically acceptable salt. Acids, which are capable of forming salts with the polypeptides, include inorganic acids such as trifluoroacetic acid (TFA) hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Bases capable of forming salts with the polypeptides include inorganic bases such as sodium hydroxide, ammonium hydroxide, potassium hydroxide and the like; and organic bases such as mono-, di- and tri-alkyl and arylamines (e.g., triethylamine, diisopropylamine, methylamine, dimethylamine and the like) and optionally substituted ethanolamines (e.g., ethanolamine, diethanolamine and the like).

The molecular probes can be used in a method to detect and/or determine the presence, location, and/or distribution of cancer cells expressing EDB-FN and/or EDA-FN, in an organ, tissue, or body area of a subject. The presence, location, and/or distribution of the molecular probe in the animal's tissue, e.g., prostate tissue, can be visualized (e.g., with an in vivo imaging modality described above). "Distribution" as used herein is the spatial property of being scattered about over an area or volume. In this case, "the distribution of cancer cells" is the spatial property of cancer cells being scattered about over an area or volume included in the animal's tissue, e.g., prostate tissue. The distribution of the molecular probe may then be correlated with the presence or absence of cancer cells in the tissue. A distribution may be dispositive for the presence or absence of a cancer cells or may be combined with other factors and symptoms by one skilled in the art to positively detect the presence or absence of migrating or dispersing cancer cells, cancer metastases or define a tumor margin in the subject.

In one aspect, the molecular probes may be administered to a subject to assess the distribution of malignant or metastatic cancer cells in a subject and correlate the distribution to a specific location. Surgeons routinely use stereotactic techniques and intra-operative MRI (iMRI) in surgical resections. This allows them to specifically identify and sample tissue from distinct regions of the tumor such as the tumor edge or tumor center. Frequently, they also sample regions of tissue on the tumor margin that are outside the tumor edge that appear to be grossly normal but are infiltrated by dispersing tumor cells upon histological examination.

Molecular probes that specifically bind to and/or complex with EDB-FN and/or EDA-FN associated with malignant or metastatic cells can be used in intra-operative imaging techniques to guide surgical resection and eliminate the "educated guess" of the location of the tumor margin by the surgeon. Previous studies have determined that more extensive surgical resection improves patient survival. Thus, molecular probes that function as diagnostic molecular imaging agents have the potential to increase patient survival rates.

In some embodiments, to identify and facilitate removal of cancers cells, microscopic intra-operative imaging (IOI) techniques can be combined with systemically administered or locally administered molecular probes described herein. The molecular probe upon administration to the subject can target and detect and/or determine the presence, location, and/or distribution of cancer cells, i.e., cancer cells associated with EDB-FN and/or EDA-FN expression, in an organ or body area of a patient. In one example, the molecular probe can be combined with IOI to identify malignant cells that have infiltrated and/or are beginning to infiltrate at a tumor margin. The method can be performed in real-time during surgery. The method can include local or systemic application of the molecular probe that includes a detectable moiety, such as a PET, fluorescent, or MRI contrast moiety. An imaging modality can then be used to detect and subsequently gather image data. The resultant image data may be used to determine, at least in part, a surgical and/or radiological treatment. Alternatively, this image data may be used to control, at least in part, an automated surgical device (e.g., laser, scalpel, micromachine) or to aid in manual guidance of surgery. Further, the image data may be used to plan and/or control the delivery of a therapeutic agent (e.g., by a micro-electronic machine or micro-machine).

Another embodiment described herein relates to a method of determining the aggressiveness or malignancy of cancer cells in a subject. It was found that the binding intensity of the molecular probes to a cancer correlated with the cancer aggressiveness. Enhanced binding correlated with more aggressive cancer whereas lower or reduced binding correlated with less aggressive or benign tumors. In one example, binding of the molecular probe to prostate tumor sections correlated with to Gleason score based on tumor aggressiveness, where enhanced binding intensity of the molecular probe correlated to aggressive or malignant prostate cancer and which was distinguished from benign prostatic hyperplasia, which displayed lower binding intensity of the probe. The methods and molecular probes described herein can be used to monitor and/or compare the aggressiveness a cancer in a subject prior to administration of a cancer therapeutic or cancer therapy, during administration, or post therapeutic regimen.

Another embodiment described herein relates to a method of monitoring the efficacy of a cancer therapeutic or cancer therapy administered to a subject. The methods and molecular probes described herein can be used to monitor and/or compare the aggressiveness, invasion, migration, dispersal, and metastases of a cancer in a subject prior to administration of a cancer therapeutic or cancer therapy, during administration, or post therapeutic regimen.

A "cancer therapeutic" or "cancer therapy", as used herein, can include any agent or treatment regimen that is capable of negatively affecting cancer in an animal, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of an animal with cancer. Cancer therapeutics can include one or more therapies such as, but not limited to, chemotherapies, radiation therapies, hormonal therapies, and/or biological therapies/immunotherapies. A reduction, for example, in cancer volume, growth, migration, and/or dispersal in a subject may be indicative of the efficacy of a given therapy. This can provide a direct clinical efficacy endpoint measure of a cancer therapeutic. Therefore, in another aspect, a method of monitoring the efficacy of a cancer therapeutic is provided. More specifically, embodiments of the application provide for a method of monitoring the efficacy of a cancer therapy.

The method of monitoring the efficacy of a cancer therapeutic can include the steps of administering in vivo to the animal a molecular probe as described herein, then visualizing a distribution of the molecular probe in the animal (e.g., with an in vivo imaging modality as described herein), and then correlating the distribution of the molecular probe with the efficacy of the cancer therapeutic. It is contemplated that the administering step can occur before, during, and after the course of a therapeutic regimen in order to determine the efficacy of a chosen therapeutic regimen. One way to assess the efficacy of the cancer therapeutic is to compare the distribution of a molecular probe pre and post cancer therapy.

In some embodiments, the molecular probe bound to and/or complexed with the EDB-FN and/or EDA-FN is detected in the subject to detect and/or provide the aggressiveness, location and/or distribution of the cancer cells in the subject. The aggressiveness, location and/or distribution of the cancer cells in the subject can then be compared to a control to determine the efficacy of the cancer therapeutic and/or cancer therapy. The control can be the location and/or distribution of the cancer cells in the subject prior to the administration of the cancer therapeutic and/or cancer therapy. The location and/or distribution of the cancer cells in the subject prior to the administration of the cancer therapeutic and/or cancer therapy can be determined by administering the molecular probe to the subject and detecting the molecular probe bound to and/or complexed with cancer cells in the subject prior to administration of the cancer therapeutic and/or cancer therapy.

In certain embodiments, the methods and molecular probes described herein can be used to measure the efficacy of a therapeutic administered to a subject for treating a metastatic or aggressive cancer. In this embodiment, the molecular probe can be administered to the subject prior to, during, or post administration of the therapeutic regimen and the distribution of cancer cells can be imaged to determine the efficacy of the therapeutic regimen. In one example, the therapeutic regimen can include a surgical resection of the metastatic cancer and the molecular probe can be used to define the distribution of the metastatic cancer pre-operative and post-operative to determine the efficacy of the surgical resection. Optionally, the methods and molecular probes can be used in an intra-operative surgical procedure, such as a surgical tumor resection, to more readily define and/or image the cancer cell mass or volume during the surgery.

In other embodiments, the targeting peptides can be conjugated to a therapeutic agent and administered to a subject for treating a cancer, such as a metastatic cancer. In this embodiment, the targeting peptides can be administered to the subject prior to, during, or post administration of the therapeutic agent and the distribution of metastatic cells can be targeted with the therapeutic agent.

The therapeutic agent can include an anti-proliferative agent that exerts an antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

In some embodiments, the targeting peptides can be coupled to the therapeutic agent using a linking molecule. The linking molecule may be a peptide linker. Alternatively, a linking molecule may be a non-peptide linker.

EXAMPLES

Example 1

We identified small peptide sequences that specifically bind to onfFN isoforms for molecular imaging of prostate cancer. Although antibodies specific to the protein has been reported in the literature, small peptides are advantageous for their lack of immunogenicity, cost effectiveness of manufacture, and readiness for translational development. In this Example, we describe a small peptide specific to EDB-FN identified by phage display. A peptide-Cy5 conjugate was synthesized for molecular imaging of the biomarker. The binding property of the peptide to EDB-EN was investigated in vitro, in vivo, and in human prostate cancer specimens using the peptide-Cy5 conjugate.
Materials and Methods
Material All reagents were used without further purification unless otherwise stated. 2-Chlorotrityl chloride resin and all of the Fmoc protected amino acids were purchased from Chem-Impex International, Inc. Fmoc-12-amino-4,7,10-trioxadodecanoic acid were purchased from EMD Chemicals Inc. (Gibbstown, N.J., USA). Sulfa-Cy5.0 NHS ester was purchased from Lumiprobe (Hallandale Beach, Fla.). Anhydrous N, N-diisopropylethyl amine (DIPEA) and N,N-dimethylformamide (DMF) were purchased from alfa Aesar (Ward Hill, Mass., USA), Trifluoroacetic acid (TEA) was purchased from Oakwood Products, Inc (West Columbia, S.C.). FastDigest enzymes for plasmid construction were purchased from Fermantas (Thermo Scientific Co., Rockford, Ill., USA)
EDB Expression with E. coli DNA sequence of EDB was optimized and synthesized (GeneArt, Regensburg, Germany) before being cloned into pQE-T7-1 expression vector (Qiagen, Valencia, Calif., USA) with NdeI and PstI restriction sites according to user's manual. Production of EDB was induced by 1 mM IPTG at the mid-log phage of growing E. coli strain BL21 (Sigma-Aldrich, St Louis, Mo., USA). Purification of EDB through 10×His tag was carried out with Ni Sepharose 6 Fast Flow (GE healthcare, Waukesha, Wis., USA), followed by dialysis against water and lyophilization. Expression and purification were evaluated with SDS-PAGE.
Phage Screening The Ph.D C7C library (New England Biolabs, Beverly, Mass., USA) was used for screen EDB specific nonapeptides. Candidate peptides were selected by carrying out panning procedures for 4 rounds. In each round, purified EDB fragment (100 μg/ml) was immobilized on non-treated 96-well plates (Corning Costar, Tewksbury, Mass., USA) with overnight coating at 4° C. 0.5% BSA was used to block non-specific binding (1 hr, room temperature) followed by incubating with phages for 1 hr at room temperature. Extensive washing with PBST (0.1%, 0.3%, 0.5% BSA, respectively, for round 1-3) was used to remove non-binding phages before eluting bound phages by 0.1M Glycine-HCl (pH 2.2) and neutralizing with Tris-HCl (pH 9.1). Eluted phages are tittered and amplified with E. coli (ER2758) according to the user's manual. Amplified phages in medium were purified by ultrafiltration and PEG/NaCl precipitation. At the end of round 4, properly diluted phages were cultured on LB/IPTG/Xgal plates and DNA from 29 randomly picked blue plaques were used for sequencing with supplied primers (New England Biolabs). Peptide sequences were resulted from translating of corresponding DNA sequences.
Peptide Synthesis ZD2 peptide with the sequence of CTVRTSADC was synthesized based on standard solid-phase synthesis from Fmoc-protected amino on a 2-chlorotrityl chloride resin. PEG (Fmoc-12-amino-4,7,10-trioxadode-canoic acid), and Sulfo-Cy5.0 NHS ester were sequentially conjugated to the N terminal of the peptide to form fluorescent ZD2 probe (ZD2-Cy5). Cyclization of the peptide was carried out by exposing the peptide to air in 10% DMSO/PBS. Purification of the cyclic peptide was done using RP-HPLC followed by lyophilization. The peptide and peptide ZD-2 conjugate were characterized by MALDI-TOF mass spectrometry.
Peptide ELISA A linear version of ZD2 (CTVRTSADA) was synthesized so that sulfhydryl group on cysteine could be used for conjugation with maleimide-activated peroxide (Sigma-Aldrich). Conjugation was carried out as instructed in the manual. The product of conjugation, ZD2-HRP, was used for peptide ELISA assay after coating a 96-well plate with purified EDB. 0.5% BSA in PBS was used to block non-specific binding for later steps. 0.39 μM to 50 μM of ZD2-HRP was incubated with coated EDB for an hour followed by extensive washing with TBST (0.1%). ABTS substrate was added subsequently and allowed to react for 30 min before the absorbance of solution in each well were measured at 415 nm. Non-coated wells added with ABTS were used as blank.

In Vitro Cellular Binding

PC3 cell line was purchased from American Type Culture Collection (ATCC, Manassas, Va., USA), and maintained in RPMI/10% FBS medium. The cells were transfected with lentivirus to express green fluorescent protein (GFP) at least 48 h prior to harvesting. To induce EMT, PC3 cells were cultured in the presence of TGFβ1 (5 ng/ml) for 5 days. For in vitro binding assay, nuclei of cells were stained with Hoechst 33342 (Life Technologies, Brooklyn, N.Y., USA) 24 h prior to adding 500 nM ZD2-Cy5. Cells were maintained in medium containing ZD2-Cy5 for 24 h and monitored with confocal microscopy. Intense shaking was avoided for live-cell binding study to retain secreted EDB-FN on the glass.

In Vivo Binding in a Mouse Tumor Model

NIH athymic male nude mice, age 4-5 weeks, were maintained at the Athymic Animal Core Facility at Case Western Reserve University according to the animal protocols approved by the Institutional Animal Care and Use Committee (IACUC). For whole-body fluorescent imaging study, a flank tumor model was constructed. Each mouse was subcutaneously implanted in both flanks with 2×10$^6$ PC3-GFP cells mixed with an equal volume of in a mixture of PBS (50 μL culture medium and 50 μL PBS). Two to three weeks after inoculation, tumors reached an average size of 0.5 cm in diameter. The mice were used for imaging with Maestro FLEX In vivo Imaging System (Cambridge Research & Instrumentation, Inc. Woburn, Mass., USA) to monitor the targeting effect of ZD2 from 0 to 24 hours. Mice were intravenously injected with ZD2-Cy5 or CERAK-Cy5 (0.3 nmol/kg body weight). After 5 h, the mice were sacrificed and the tumor and various organs were imaged with the Maestro FLEX In vivo Imaging System.

Histological Staining of Human Prostate Sections

Human prostate sections were acquired from OriGene (Rockville, Md., USA). Antibodies used in this study include mouse monoclonal anti-Fibronectin antibody (BC-1, ab154210, Abcam, Cambridge, UK), Rhodamine-Red-X conjugated goat polyclonal anti-rabbit IgG (H+L) (Jackson Immuno Research Lab. West Grove, Pa., USA), and FITC conjugated goat polyclonal anti-mouse Fc (ab97264, Abcam). Frozen tissue section (5 nm) imbedded in OCT was used for immunostaining and peptide staining. Paraffin embedded samples were de-paraffinized and processed with antigen retrieval using general methods. Sections were permeabilized and fixed with cold acetone followed by 0.5% BSA blocking for 1 hr at room temperature. Peptide staining was carried at the concentration of 5 uM. Slides were counter-stained with DAPI and mounted with coverslip using Prolong Gold regent (Invitrogen) before imaging. Stained tissue was imaged on an Olympus FV1000 confocal laser scanning microscope. GFP was observed using 405 nm laser and the emission wavelength was read from 480 to 495 nm and represented as green. DAPI was observed using 405 nm laser and the emission wavelength was read from 450 to 470 nm and expressed as blue. Cy5.0 was observed using 635 nm laser and the emission wavelength was read from 655 to 755 nm and expressed as red.

qPCR

Total RNA was collected from cell samples and isolated using an RNeasy Plus Kit (Qiagen). RNA was then reversely transcribed into cDNA using the High Capacity cDNA Transcription Kit (Applied Biosystems, Foster City, Calif.). Semiquantitative real-time PCR was carried out using a SYBR Green Master Mix (Life Technologies) according to the manufacturer's recommendations. RNA concentration for individual genes examined was normalized to their corresponding GAPDH RNA signals. Both cDNA synthesis and real-time PCR were carried out on the Mastercycler realplex2 (VWR International, West Chester, Pa., USA). Relative mRNA expression levels were calculated using the $2^{-\Delta\Delta C_T}$ method. The oligonucleotide primer pair sequences were 5'-GCAGCCCACAGTGGAGTAT-3' (SEQ ID NO: 31) for EDB sense and 5'-GGA GCAAGGTTGATTTCTTT-3' (SEQ ID NO: 32) for antisense, 5'-GCAGCCCACAGTG-GAGTAT-3' (SEQ ID NO: 33) for EDA sense and 5'-GGA GCAAGGTTGATTTCTTT-3' (SEQ ID NO: 34) for antisense, 5'-ACCCAGAAGACTGTGGATGG-3' (SEQ ID NO: 35) for GAPDH sense and 5'-TCTAGACGGCAG-GTCAGGTC-3' (SEQ ID NO:36) for antisense, 5'-TGC-CCAGAAAATGAAAAAGG-3' (SEQ ID NO: 37) for E-cadherin sense and 5'-GTGTATGTGGCAATGCGTTC-3' (SEQ ID NO: 38) for antisense, and 5'-ACAGTGGCCAC-CTACAAAGG-3' (SEQ ID NO: 39) for N-cadherin sense and 5'-CCGAGATGGGGTTGATAATG-3' (SEQ ID NO: 40) for antisense. The primers were purchased from Invitrogen.

Western Blot

Tissues from mice were lysed with T-PER Tissue Protein Extraction Reagent (Thermo scientific) supplemented with PMSF (Sigma) and protease inhibitors (Sigma) according to manufacturer's instructions. Human prostate lysates were acquired from OriGene and used under manufacturer's instruction. 20 μg proteins were loaded for electrophoresis and blotting. Gels, PVDF membranes and other related reagents were purchased from Biorad (Hercules, Calif., USA) and used according to manufacturer's instructions. General Electric Typhoon Phosphor imager was used for processing membrane blotted with FITC conjugated secondary antibody.

Statistical Analysis

All data are presented as mean±SEM except stated. When two groups were compared, the two-tailed Student's t test was used ($p<0.05$ was considered significant).

Results

EDB-FN Binding Peptide

EDB is a type-III-homology repeat with a sequence of 91 amino acids encoded by a single exon, which are identical in vertebrates. The EDB fragment was expressed in *E. coli* by cloning codon optimized DNA sequence of EDB into an expression plasmid, pQE-T7-1, under the regulation of T7 promoter, as shown in FIG. 1A. The ligation of EDB DNA in the plasmid was verified by DNA sequencing. Expression and purification of EDB fragment were confirmed by SDS-PAGE as shown in FIG. 1B. A M13 phage library displaying cyclic nonapeptide flanked by two cysteine residues on its pIII protein was used for screening EDB binding peptides. Four rounds of panning yielded an enriched phage library containing phages with high EDB binding ability, which was determined by phage ELISA assay. Out of 29 identified phage clones, the peptide sequence of CTVRTSADC (SEQ ID NO: 10) appeared 5 times and was named ZD2.

Cyclic ZD2 peptide (CTVRTSADC) (SEQ ID NO: 10) was synthesized using standard solid phase peptide chemistry and was characterized by MALDI-TOF mass spectrometry (FIG. 1C). The peptide was then labeled with a fluorescence chromophore cyanine 5 (Cy5) through a short PEG linker ($NH_2$—$(CH_2CH_2O)_3$—$CH_2CH_2COOH$) to give a peptide fluorescence probe ZD2-Cy5. The peptide was also conjugated to peroxidase (ZD2-HRP) and the binding affinity of the peptide to EDB fragment was determined using peptide ELISA assay. FIG. 1D shows the concentration-dependent binding curve of ZD2-HRP to the EDB fragment, which gave the binding affinity ($K_D$, the equilibrium dissociation constant) of 4.52±2.68 μM between ZD2-HRP and EDB.

In Vitro Peptide Binding to EDB-FN Excreted by TGFβ1-Induced PC3 Cancer Cells

Elevated expression of onfFN is a marker of EMT of prostate cancer cells. The treatment of PC3 human prostate cancer cells with TGFβ1 resulted in an elongated mesenchymal phenotype as compared with cells without induction, as shown in FIG. 2A. Up-regulation of EDB-FN expression was companied with E-Cad down-regulation and N-Cad up-regulation as determined by quantitative PCR (FIG. 2B). As a result, ZD2-Cy5 showed substantially more binding to the periphery of the PC3 cells treated with TGFβ1 than the untreated cells because of the production and secretion of EDB-FN by the TGFβ1-induced cells as shown in FIG. 2C.

In Vivo Binding of ZD2-Cy5 in a Mouse PC3 Prostate Tumor Model

Whole-body fluorescence imaging of mice bearing PC3-GFP flank tumor xenografts showed significantly high accumulation of ZD2-Cy5 tumor (FIG. 3A). Tumor of mice injected with ZD2-Cy5 was clearly highlighted in the Cy5 fluorescence image at 1.5 h after intravenous injection. Relatively high tumor to normal (T/N) ratio of Cy5 signal could be maintained for up to 24 hours for mice injected with ZD2-Cy5, compared with mice injected with a non-specific control CERAK-Cy5 (FIG. 3B). Tumor and major organs were collected to image the Cy5 signal 5 hours after injection. The result verified the specific accumulation of Cy5 labeled ZD2 in tumor, while little tumor accumulation was seen for mice injected with CERAK-Cy5 (FIG. 3C). Western blot analysis of protein lysates from tumor, liver, and lung indicated that PC3 tumor expresses substantially more EDB-FN than in the liver and lung, as shown in FIG. 3D.

Imaging of the tissue sections from the tumor bearing mice injected with ZD2-Cy5 or CERAK-Cy5 further verified the specific binding of ZD2-Cy5 in the tumor, and the Cy5 signal was distributed in the ECM of the tumor. Little accumulation of ZD2-Cy5 was found in the liver or lung (FIG. 4A). Since EDB-FN is a biomarker for angiogenesis, we did immunofluorescence staining on those tumor sections using antibodies specific to EDB-FN and CD31. BC-1 was chosen as a reference to correlate ZD2 distribution with EDB-FN expression, while anti-CD31 antibody was used to correlate angiogenesis. Immunofluorescence images in FIG. 4B confirmed the overlap between ZD2-Cy5 binding with both FN expression and angiogenesis.

ZD2-Cy5 Binding in Prostate Cancer of Different Aggressiveness

The binding activity of ZD2-Cy5 was further assessed in human prostate tumor sections of different Gleason scores. A human prostate BPH section was used as a control. As shown in FIG. 5A and FIG. 5C, tumor with high Gleason score exhibited strong staining with ZD2-Cy5 in both stromal and glandular areas, while normal glands were unstained. Similar trend was also observed with BC-1 immunofluorescence staining. Histogram analysis of Cy5 fluorescence images acquired from the ZD2 stained sections indicated a shift of pixel value distribution from low intensity values to high intensity values as the Gleason score of tumor increases from GS 7 to GS 9 (FIG. 5B). In histogram analysis, measuring the pixel intensity ranging from 50 to 255 on the 8-unit images clarified the increase in ZD2 binding on sections of higher Gleason score. Protein lysates from normal prostate and cancerous prostate (GS=3+4) were also analyzed with Western blot in order to confirm the high expression of EDB-FN in cancer samples (FIG. 5D). Competitive staining by blocking sections with BC-1 inhibited the tumor binding ZD2-Cy5 (FIG. 5E). This result indicates that BC-1 and ZD2 share the same molecular target.

We have identified cyclic nonapeptide ZD2 with good binding affinity to EDB-FN using phage display. The binding specificity of the peptide was first verified using a fluorescence probe ZD2-Cy5 in vitro in post-EMT PC3 prostate cancer cells. ZD2-Cy5 showed strong binding of in post-EMT PC3 cells and non-binding in uninduced cells. Strong binding of ZD2-Cy5 to induced PC3 cells was localized at cell periphery, which was in agreement with the fact that FN was an ECM protein. EMT induction of PC3 cells by TGFβ1 resulted in substantial up-regulation of EDB-FN in post-EMT PC3 prostate cancer cells and strong binding. EMT is generally associated with invasive cancer types. The results suggest that EDB-FN is a potential biomarker of aggressive prostate cancer and ZD2 peptide is a viable probe for the biomarker. The tumor binding specificity was further demonstrated in mice bearing PC3-GFP prostate cancer xenografts.

The binding activity of ZD2 was further tested in human prostate tumor sections of different Gleason score. Gleason score is the most commonly used pathological grading system in clinical management of prostate cancer. Our histological staining experiment showed that ZD2-Cy5 had strong binding prostate tumors (GS7 and GS9), not in BPH tumor sections. The binding intensity of ZD2-Cy5 in the tumor sections appears correlated to Gleason score based tumor aggressiveness, which is in agreement with the previous study that showed an overexpression of EDB-FN in prostate carcinoma compared with BPH. The results suggest EDB-FN as a desirable marker for differentiating prostate cancer from BPH.

Currently, the needle-biopsy Gleason scoring is routinely used in the risk-stratified management of prostate cancer and decision making. The goal of this risk-stratified management strategy is to minimize the treatment-related harm to patients who do not benefit from treatment. However, the accuracy of diagnostic procedure is often compromised by the heterogeneity of cancer within the same prostate and the inadequacy of prostate sampling from needle-biopsy. Therefore, a molecular imaging technology with the potential of non-invasively mapping the aggressiveness of prostate cancer throughout the prostate is advantageous over invasive biopsy and could provide more accurate differential diagnosis. A number of molecular targets have been tested for prostate cancer molecular diagnosis. For example, cell-surface biomarkers PSMA, N-Cadherin and hepsin, and intracellular markers DD3/PCA3 and GalNAc-T3 have been investigated as markers for prostate cancer. However, it is still uncertain whether these targets could be used as indicators for cancer aggressiveness. EDB-FN is a molecular marker prostate cancer angiogenesis and EMT, characteristics of cancer aggressiveness. Molecular imaging EDB-FN could provide non-invasive differential diagnosis of prostate cancer. The abundant expression of EDB-FN in tumor ECM would be more accessible to molecular probes, which lead to improved binding of imaging probe.

Example 2

In this Example, we developed an EDB-FN targeted contrast agent, l-ZD2-Gd(HP-DO3A) for molecular imaging of micrometastases. This contrast agent is rationally designed based on an EDB targeting peptide, ZD2, discovered by phage display technique. The linear version of this peptide, l-ZD2, has been evaluated for its targeting capacity. A modular system for gadolinium complexation is used in conjugation with l-ZD2. This small gadolinium-based contrast agent targets to EDB-FN secreted by cancer cells and fibroblasts, etc., with minimal accumulation in normal tissues. Overexpression of EDB-FN in cellular level may considerably contribute to early and sensitive detection of micrometastases. In this Example, we assessed the effectiveness of l-ZD2-Gd(HP-DO3A) in detecting micrometastases at early stage following tumor inoculation. These results demonstrate that EDB-FN targeted contrast agent can more efficiently detect micrometastases with a smaller size, thus increasing detecting sensitivity for a better diagnosis.

The Use of Linear ZD2 for EDB-FN Targeting

We previously reported the discovery of a cyclic nonapeptide, ZD2 (CTVRTSADC) (SEQ ID NO: 10) that specifically targets EDB-FN. However, cyclization of ZD2 with disulfide bond tends to complicate further chemical modification with the possibility of intermolecular linkage. Thus, we assessed the capability of the linear version, l-ZD2 (TVRTSAD) (SEQ ID NO: 1), with the expectation that l-ZD2 would perform similarly to cyclic ZD2. To measure binding affinity between l-ZD2 and EDB protein, the peptide with a sequence of $NH_2$-TVRTSADC-COOH (SEQ ID NO: 41) is synthesized in solid phase. The thiol group on the cysteine is used to conjugate maleimide activated horseradish peroxidase (HRP), resulting in l-ZD2-HRP. Similarly, CERAK-HRP is synthesized as a control. ELISA (Enzyme linked immunosorbent assay) showed that l-ZD2-HRP bound to EDB protein with an affinity of xxx $\mu mol^{-1}$, which is comparable to cyclic ZD2 with a slight increase in affinity, while CERAK-HRP showed no observable binding to EDB. No binding between l-zd2-HRP and EDA was seen. Since it is believed that cyclized peptide possesses more structural stableness in vivo, we evaluated the stableness of l-ZD2 in human serum within 24 hours with HPLC. No degradation was seen of l-ZD2 at 24 hours from the spectrum. Therefore, we can conclude that the linear version of ZD2 can also be used for EDB-FN targeting.

Upregulation of EDB-FN is a Hallmark of Breast Cancer Metastasis

4T1 cells have been shown to upregulate fibronectin expression as a result of transforming growth factor-beta (TGFβ) induction. TGFβ is a key regulator of epithelial-to-mesenchymal transition (EMT), which is believed as the driving force of metastasis. To demonstrate the use of EDB-FN as a biomarker for metastases targeting, we compared the mRNA level of EDB-FN in normal 4T1 cells and 4T1 cells with 5 days of TGFβ induction. Notably, there is a three-fold upregulation of EDB-FN in 4T1 cells as a result of TGFβ induction. (FIG. 6A). Western blot analysis of protein extracts of metastatic tumors from different organ compared with primary tumor also showed the upregulation of EDB-FN in tissue level. (FIG. 6B). Minimal EDB-FN expression is seen in normal tissues, such as brain, lung and liver. Together, these results supported the hypothesis that EDB-FN can be used as an efficient biomarker for targeting metastatic tumors.

As tumor cells produce EDB-FN to promote its migration, we further validated if Cy5 labeled l-ZD2 (l-ZD2-Cy5) can bind to TGFβ induced 4T1 cells in vitro. Our result suggested that l-ZD2-Cy5 is bound to induced 4T1 cells within 3 hours, but no binding between CREKA-Cy5 on induced 4T1 cells was seen. To explain this, we hypothesize that in this form of cell culture, no clot formation can take action to provide binding sites for CREKA-Cy5. To validate our hypothesis, we further produced a 3D culture system that mimics the "soil" of metastatic tumor. In the 3D culture system, 4T1 cells were cultured in a microenvironment containing TGFβ, collagen, and fibrin. It was found out that 1-ZD2-Cy5 accumulated in the cell periphery starting from day 1. In overall, these evidences point to the conclusion that the use of EDB-FN for targeting micrometastasis may be advantageous compared with Fibronectin-Fibrin complexes in that EDB-FN appears earlier than Fibronectin-Fibrin in the pre-metastatic niche.

Design of an EDB-FN Targeted Gadolinium-Based Magnetic Resonance Probe

The design of the EDB-FN targeted MRI agent was based on a modular system that forms small molecular contrast agent in conjugation with l-ZD2. Compound 1 in FIG. 7A was prepared by adding a short PEG linker, followed by reacting with 5-hexynoic acid, resulting in an alkyne group for conjugation through click chemistry. The final product from reaction of compound 1 and 2 was purified with HPLC and characterized with Maldi-Tof spectrum. (FIG. 7B) Measurement of relaxivities (T1 and T2) showed that the resulting compound possess relatively high relaxivities at 3T (FIG. 7C).

Figure 8A:
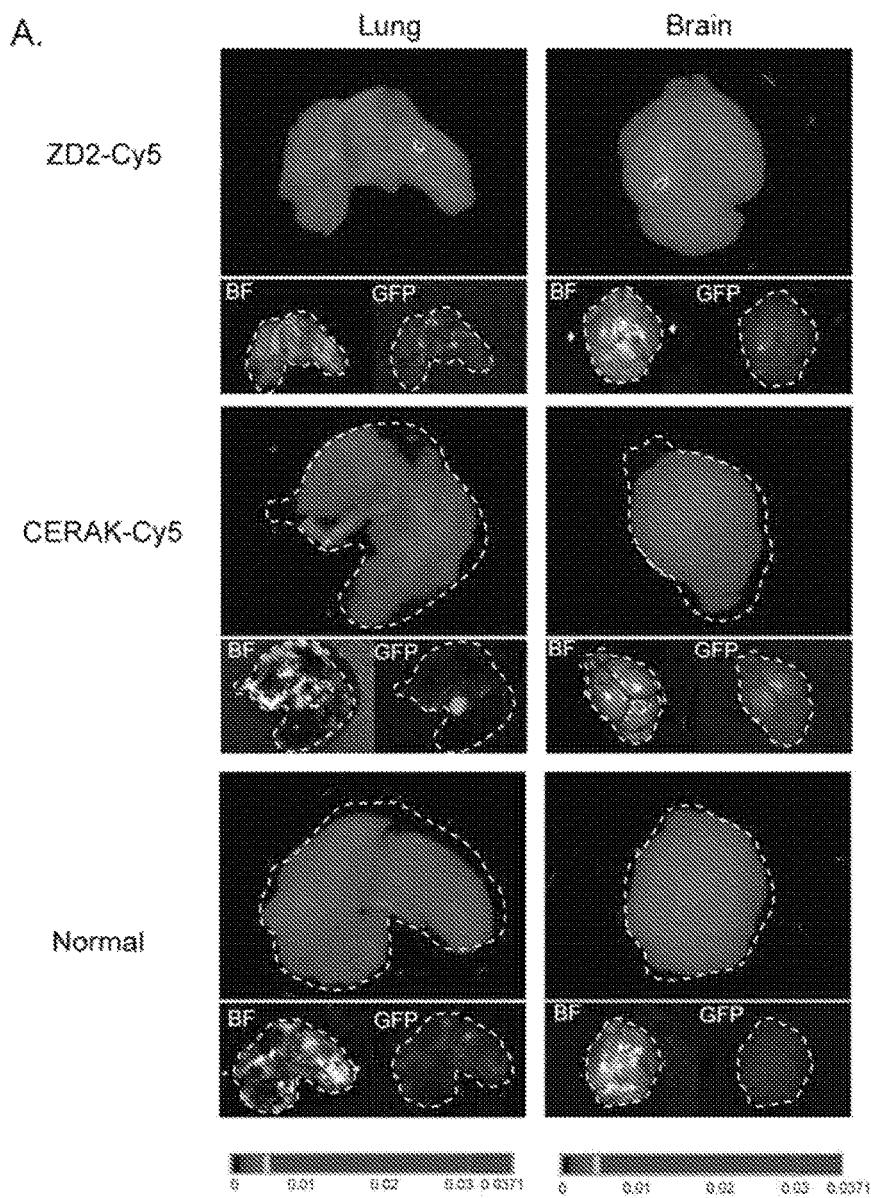
FIGS. 8(A-C) illustrate A) Bright field, GFP and Cy5 images of lung and brain harvested from mice injected with ZD2-Cy5 or CREKA-Cy5. Normal mice bearing no tumors were used as a control. Cy5 signal was presented with jetblack colormap. Display keys for the colormaps of each group were shown in below. B) Maestro fluorescent images of muscle, lymph node metastatic tumor (LN Mets), and adrenal gland tumor (AG Mets). Cy5 signal was represented with jetblack colormap. Display keys were shown in below. GFP images were also shown. C) Confocal microscopic images of the cryosections of tumor from mice injected with l-ZD2-Cy5. Nucleus staining (DAPI, a), GFP (b), Cy5 (c), and merged images were shown.

In Vivo Detection of Micrometastasis with l-Zd2-Cy5 in a Breast Cancer Metastatic Tumor Model In order to construct a metastatic tumor model, $0.2 \times 10^6$ 4T1 tumor cells undergone 5 days of TGFβ induction were injected through left ventricle of heart, resulting in the spread of tumor cells primarily in brain, lung, liver, lymph node, adrenal gland, chest, and bone marrow. Bioluminescent images of the mice at two weeks were used to monitor the growth of tumors. To assess the targeting capacity of l-ZD2-Cy5, brain and lung were harvested from the mice three hours after 10 nmol l-ZD2-Cy5 were injected. Signal from l-ZD2-Cy5 clearly outlined the micrometastases grown on brain and lung, with GFP signal from 4T1 consolidating the positions of tumors. (FIG. 8A) CERAK-Cy5, in contrary, didn't show binding on small metastatic tumors. Normal brain and lung harvested from normal mice injected with l-ZD2-Cy5 were used as negative controls. Examination of bigger metastatic tumors in lymph nodes and adrenal gland, as shown in FIG. 8B further backed up the targeting efficiency of l-ZD2-Cy5. Confocal laser scanning microscopy of cryosectioned tumor demonstrated that l-ZD2-Cy5 distributed in the ECM of the cells and forms a fibrillary network. Together, these results pave the path towards testing MRI probe based on 1-zd2 for in vivo imaging of metastasis.

In Vivo Magnetic Resonance Imaging of Breast Cancer Metastasis with l-ZD2-Gd(HP-DO3A)

Figure 9A:
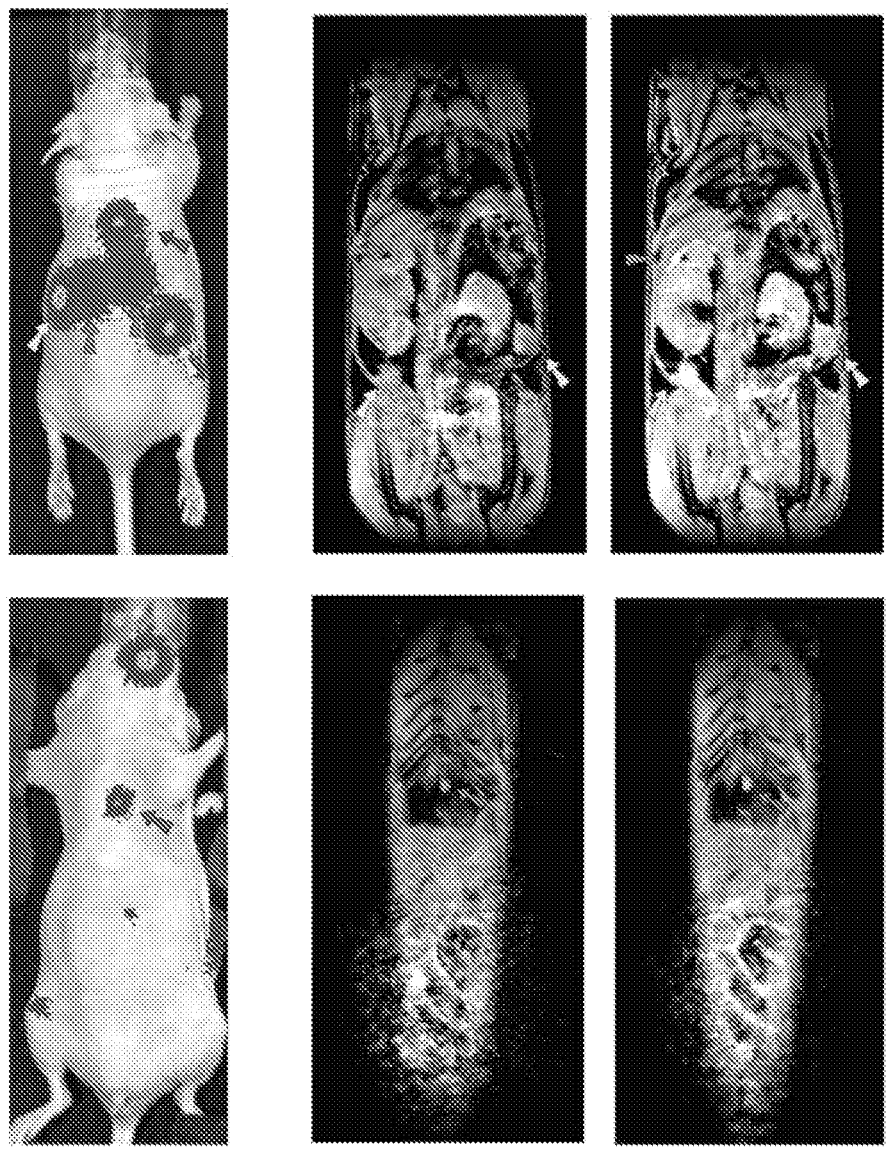
FIGS. 9(A-C) illustrate: A) Bioluminescent images of a representative mouse developed metastatic tumors in lymph nodes, adrenal glands, and chest and corresponding tumors identified in MRI images. B) Colocalization of MRI and BLI to verify the targeting of l-zd2-Gd(HP-DO3A) to metastatic tumors on different organs. C. MRI of metastatic tumor of CERAK-Gd(HP-DO3A).

Breast cancer metastatic tumor model was imaged at two weeks in order to validate the properties of l-ZD2-Gd(HP-DO3A) in detecting breast cancer micrometastases. In FIG. 9A, a mouse developed with metastatic tumors in lymph nodes, adrenal glands, and chest was imaged in MRI after l-ZD2-Gd(HP-DO3A) injection, in conjugation with BLI validation of tumor positions. All five tumors indicated in BLI showed enhancement in MRI, with all the tumor positions accurately reflected. Representative images of tumors in the leg, shoulder, and lung were shown in FIG. 9B. Imaging of mice injected with CERAK-Gd(HP-DO3A) showed minimal tumor enhancement. CNR measurement of tumor, liver, kidney, bladder, and muscle demonstrated a significant higher signal enhancement of l-ZD2-Gd(HP-DO3A) in tumor (FIG. 9C).

Figure 10:
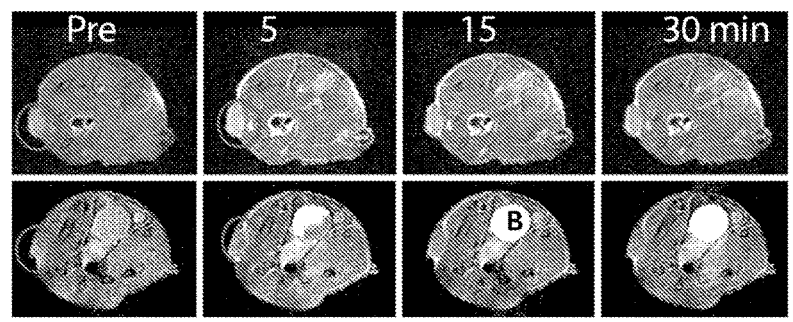
FIG. 10 illustrates T1-weighted 2D axial spin-echo MR images before (pre) and at 5, 15, 30 min after i.v. injection of ZD2-Gd(HP-DO3A) and Gd-(HP-DO3A) at 0.1 mmol-Gd/kg in mice bearing PC-3 prostate cancer xenograft. Circle, tumor; B, bladder.

The same contrast agent also works for prostate cancer imaging. We then tested the effectiveness of targeting EDB-FN with the contrast agent for prostate cancer MRI in male nude mice bearing primary PC-3 human prostate cancer xenograft. As shown in FIG. 10, the targeted agent produced robust tumor enhancement for at least 30 min after intravenous injection at a dose of 0.1 mmol-Gd/kg, while a clinical control Gd(HP-DO3A) generated little contrast enhancement under in the tumor under the same condition. The result indicates that the small molecular peptide targeted contrast agent specific to EDB-FN in tumor ECM is effective for contrast enhanced MRI of prostate cancer and EDB-FN is a viable molecular target for non-invasive detection of prostate cancer with molecular MRI.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A molecular probe for use in detecting, monitoring, and/or imaging cancer cells and/or cancer cell aggressiveness, the molecular probe comprising:
    at least one targeting peptide coupled to a detectable moiety, the targeting peptide binding to EDB-FN or EDA-FN and comprising at least one amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30.

2. The probe of claim 1, the detectable moiety comprising an imaging agent and the probe being detectable upon administration to a subject by at least one of gamma imaging, positron emission tomography (PET) imaging, computer tomography (CT) imaging, magnetic resonance imaging, near infrared imaging, or fluorescent imaging.

3. The probe of claim 1, the detectable moiety including at least one of an optical dye, MRI contrast agent, a PET agent, a SPECT agent, a CT contrast agent, radiolabel, or an ultrasound contrast agent.

4. The probe of claim 1, the at least one targeting peptide being covalently linked to the detectable moiety.

5. The probe of claim 1, further comprising a linker that couples the targeting peptide to the detectable moiety.

6. The probe of claim 5, wherein the linker is a peptide linker or polymer linker.

7. A method comprising:
   contacting a tissue of a subject with a molecular probe comprising at least one targeting peptide coupled to a detectable moiety, the targeting peptide binding to EDB-FN or EDA-FN and comprising at least one amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30; and
   detecting the molecular probes in the tissue of the subject.

8. The method of claim 7, determining the location and/or distribution of cancer cells in the tissue by detecting the molecular probes.

9. The method of claim 7, wherein the contacting step is in vivo, ex vivo, or in vitro.

10. The method of claim 7, the detectable moiety comprising an imaging agent and the probe being detectable upon administration to the subject by at least one of gamma imaging, positron emission tomography (PET) imaging, computer tomography (CT) imaging, magnetic resonance imaging, near infrared imaging, or fluorescent imaging.

11. The method of claim 7, the detectable moiety including at least one of an optical dye, MRI contrast agent, a PET agent, a SPECT agent, a CT contrast agent, radiolabel, or an ultrasound contrast agent.

12. The method of claim 7, the at least one targeting peptide being covalently linked to the detectable moiety.

13. The method of claim 7, further comprising a linker that couples the targeting peptide to the detectable moiety.

14. The method of claim 13, wherein the linker is a peptide linker or polymer linker.

15. The method of claim 7, the probe being systemically administered to a subject having or suspected of having cancer.

16. The method of claim 15, the cancer comprising at least one of breast cancer, liver cancer, stomach cancer, colon cancer, pancreatic cancer, ovarian cancer, lung cancer, kidney cancer, prostate cancer, testicular cancer, glioblastoma, sarcoma, bone cancer, brain cancer, head and neck cancers, or skin cancer.

17. The method of claim 7, the subject having cancer and the probe being administered to the tissue of the subject to determine cancer aggressiveness.

18. A method of detecting cancer cells in a subject having or suspected of having cancer, the method comprising:
   administering to the subject a molecular probe comprising at least one targeting peptide coupled to a detectable moiety, the targeting peptide binding to EDB-FN or EDA-FN and comprising at least one amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, and SEQ ID NO: 30; and
   detecting the molecular probes in the subject to determine the location and/or distribution of the cancer cells in the subject.

19. The method of claim 18, the detectable moiety comprising an imaging agent and the probe being detectable upon administration to the subject by at least one of gamma imaging, positron emission tomography (PET) imaging, computer tomography (CT) imaging, magnetic resonance imaging, near infrared imaging, or fluorescent imaging.

20. The method of claim 18, the detectable moiety including at least one of an optical dye, MRI contrast agent, a PET agent, a SPECT agent, a CT contrast agent, radiolabel, or an ultrasound contrast agent.

21. The method of claim 18, the probe being systemically administered to a subject having or suspected of having cancer.

22. The method of claim 18, the cancer comprising at least one of breast cancer, liver cancer, stomach cancer, colon cancer, pancreatic cancer, ovarian cancer, lung cancer, kidney cancer, prostate cancer, testicular cancer, glioblastoma, sarcoma, bone cancer, brain cancer, head and neck cancers, or skin cancer.

* * * * *

SEQUENCE LISTING

```
<160> NUMBER OF SEQ ID NOS: 41

<210> SEQ ID NO 1
<211> LENGTH: 7
<212> TYPE: PRT
<213> ORGANISM: Homo sapiens

<400> SEQUENCE: 1

Thr Val Arg Thr Ser Ala Asp
1               5

<210> SEQ ID NO 2
<211> LENGTH: 7
<212> TYPE: PRT
<213> ORGANISM: Homo sapiens

<400> SEQUENCE: 2

Asn Trp Gly Asp Arg Ile Leu
1               5

<210> SEQ ID NO 3
<211> LENGTH: 7
<212> TYPE: PRT
<213> ORGANISM: Homo sapiens

<400> SEQUENCE: 3

Asn Trp Gly Lys Pro Ile Lys
1               5

<210> SEQ ID NO 4
<211> LENGTH: 7
<212> TYPE: PRT
<213> ORGANISM: Homo sapiens

<400> SEQUENCE: 4

Ser Gly Val Lys Ser Ala Phe
1               5

<210> SEQ ID NO 5
<211> LENGTH: 7
<212> TYPE: PRT
<213> ORGANISM: Homo sapiens

<400> SEQUENCE: 5

Gly Val Lys Ser Tyr Asn Glu
1               5

<210> SEQ ID NO 6
<211> LENGTH: 7
<212> TYPE: PRT
<213> ORGANISM: Homo sapiens

<400> SEQUENCE: 6

Ile Gly Lys Thr Asn Thr Leu
1               5
```

```
<210> SEQ ID NO 7
<211> LENGTH: 7
<212> TYPE: PRT
<213> ORGANISM: Homo sapiens

<400> SEQUENCE: 7

Ile Gly Asn Ser Asn Thr Leu
1               5

<210> SEQ ID NO 8
<211> LENGTH: 7
<212> TYPE: PRT
<213> ORGANISM: Homo sapiens

<400> SEQUENCE: 8

Ile Gly Asn Thr Ile Pro Val
1               5

<210> SEQ ID NO 9
<211> LENGTH: 7
<212> TYPE: PRT
<213> ORGANISM: Homo sapiens

<400> SEQUENCE: 9

Leu Tyr Ala Asn Ser Pro Phe
1               5

<210> SEQ ID NO 10
<211> LENGTH: 9
<212> TYPE: PRT
<213> ORGANISM: Homo sapiens

<400> SEQUENCE: 10

Cys Thr Val Arg Thr Ser Ala Asp Cys
1               5

<210> SEQ ID NO 11
<211> LENGTH: 9
<212> TYPE: PRT
<213> ORGANISM: Homo sapiens

<400> SEQUENCE: 11

Cys Asn Trp Gly Asp Arg Ile Leu Cys
1               5

<210> SEQ ID NO 12
<211> LENGTH: 9
<212> TYPE: PRT
<213> ORGANISM: Homo sapiens

<400> SEQUENCE: 12

Cys Asn Trp Gly Lys Pro Ile Lys Cys
1               5

<210> SEQ ID NO 13
<211> LENGTH: 9
<212> TYPE: PRT
<213> ORGANISM: Homo sapiens

<400> SEQUENCE: 13

Cys Ser Gly Val Lys Ser Ala Phe Cys
1               5
```

```
<210> SEQ ID NO 14
<211> LENGTH: 9
<212> TYPE: PRT
<213> ORGANISM: Homo sapiens

<400> SEQUENCE: 14

Cys Gly Val Lys Ser Tyr Asn Glu Cys
1               5

<210> SEQ ID NO 15
<211> LENGTH: 9
<212> TYPE: PRT
<213> ORGANISM: Homo sapiens

<400> SEQUENCE: 15

Cys Ile Gly Lys Thr Asn Thr Leu Cys
1               5

<210> SEQ ID NO 16
<211> LENGTH: 9
<212> TYPE: PRT
<213> ORGANISM: Homo sapiens

<400> SEQUENCE: 16

Cys Ile Gly Asn Ser Asn Thr Leu Cys
1               5

<210> SEQ ID NO 17
<211> LENGTH: 9
<212> TYPE: PRT
<213> ORGANISM: Homo sapiens

<400> SEQUENCE: 17

Cys Ile Gly Asn Thr Ile Pro Val Cys
1               5

<210> SEQ ID NO 18
<211> LENGTH: 9
<212> TYPE: PRT
<213> ORGANISM: Homo sapiens

<400> SEQUENCE: 18

Cys Leu Tyr Ala Asn Ser Pro Phe Cys
1               5

<210> SEQ ID NO 19
<211> LENGTH: 7
<212> TYPE: PRT
<213> ORGANISM: Homo sapiens

<400> SEQUENCE: 19

Trp Asn Tyr Pro Phe Arg Leu
1               5

<210> SEQ ID NO 20
<211> LENGTH: 7
<212> TYPE: PRT
<213> ORGANISM: Homo sapiens

<400> SEQUENCE: 20

Ser Asn Thr Ser Tyr Val Asn
1               5

<210> SEQ ID NO 21
<211> LENGTH: 7
```

```
<212> TYPE: PRT
<213> ORGANISM: Homo sapiens

<400> SEQUENCE: 21

Ser Phe Ser Tyr Thr Ser Gly
1               5

<210> SEQ ID NO 22
<211> LENGTH: 7
<212> TYPE: PRT
<213> ORGANISM: Homo sapiens

<400> SEQUENCE: 22

Trp Ser Pro Ala Pro Met Ser
1               5

<210> SEQ ID NO 23
<211> LENGTH: 7
<212> TYPE: PRT
<213> ORGANISM: Homo sapiens

<400> SEQUENCE: 23

Thr Arg Glu His Pro Ala Gln
1               5

<210> SEQ ID NO 24
<211> LENGTH: 7
<212> TYPE: PRT
<213> ORGANISM: Homo sapiens

<400> SEQUENCE: 24

Ala Arg Ile Ile Asp Asn Ala
1               5

<210> SEQ ID NO 25
<211> LENGTH: 9
<212> TYPE: PRT
<213> ORGANISM: Homo sapiens

<400> SEQUENCE: 25

Cys Trp Asn Tyr Pro Phe Arg Leu Cys
1               5

<210> SEQ ID NO 26
<211> LENGTH: 9
<212> TYPE: PRT
<213> ORGANISM: Homo sapiens

<400> SEQUENCE: 26

Cys Ser Asn Thr Ser Tyr Val Asn Cys
1               5

<210> SEQ ID NO 27
<211> LENGTH: 9
<212> TYPE: PRT
<213> ORGANISM: Homo sapiens

<400> SEQUENCE: 27

Cys Ser Phe Ser Tyr Thr Ser Gly Cys
1               5

<210> SEQ ID NO 28
<211> LENGTH: 9
<212> TYPE: PRT
<213> ORGANISM: Homo sapiens
```

<400> SEQUENCE: 28

Cys Trp Ser Pro Ala Pro Met Ser Cys
1               5

<210> SEQ ID NO 29
<211> LENGTH: 9
<212> TYPE: PRT
<213> ORGANISM: Homo sapiens

<400> SEQUENCE: 29

Cys Thr Arg Glu His Pro Ala Gln Cys
1               5

<210> SEQ ID NO 30
<211> LENGTH: 9
<212> TYPE: PRT
<213> ORGANISM: Homo sapiens

<400> SEQUENCE: 30

Cys Ala Arg Ile Ile Asp Asn Ala Cys
1               5

<210> SEQ ID NO 31
<211> LENGTH: 19
<212> TYPE: DNA
<213> ORGANISM: Homo sapiens

<400> SEQUENCE: 31
gcagcccaca gtggagtat                                             19

<210> SEQ ID NO 32
<211> LENGTH: 20
<212> TYPE: DNA
<213> ORGANISM: Homo sapiens

<400> SEQUENCE: 32
ggagcaaggt tgatttcttt                                            20

<210> SEQ ID NO 33
<211> LENGTH: 19
<212> TYPE: DNA
<213> ORGANISM: Homo sapiens

<400> SEQUENCE: 33
gcagcccaca gtggagtat                                             19

<210> SEQ ID NO 34
<211> LENGTH: 20
<212> TYPE: DNA
<213> ORGANISM: Homo sapiens

<400> SEQUENCE: 34
ggagcaaggt tgatttcttt                                            20

<210> SEQ ID NO 35
<211> LENGTH: 20
<212> TYPE: DNA
<213> ORGANISM: Homo sapiens

<400> SEQUENCE: 35
acccagaaga ctgtggatgg                                            20

-continued

```
<210> SEQ ID NO 36
<211> LENGTH: 20
<212> TYPE: DNA
<213> ORGANISM: Homo sapiens

<400> SEQUENCE: 36
tctagacggc aggtcaggtc                                                     20

<210> SEQ ID NO 37
<211> LENGTH: 20
<212> TYPE: DNA
<213> ORGANISM: Homo sapiens

<400> SEQUENCE: 37
tgcccagaaa atgaaaaagg                                                     20

<210> SEQ ID NO 38
<211> LENGTH: 20
<212> TYPE: DNA
<213> ORGANISM: Homo sapiens

<400> SEQUENCE: 38
gtgtatgtgg caatgcgttc                                                     20

<210> SEQ ID NO 39
<211> LENGTH: 20
<212> TYPE: DNA
<213> ORGANISM: Homo sapiens

<400> SEQUENCE: 39
acagtggcca cctacaaagg                                                     20

<210> SEQ ID NO 40
<211> LENGTH: 20
<212> TYPE: DNA
<213> ORGANISM: Homo sapiens

<400> SEQUENCE: 40
ccgagatggg gttgataatg                                                     20

<210> SEQ ID NO 41
<211> LENGTH: 9
<212> TYPE: PRT
<213> ORGANISM: Homo sapiens

<400> SEQUENCE: 41

Thr Val Arg Thr Ser Ala Asp Cys Cys
1               5
```